(12) United States Patent
Polonskiy et al.

(10) Patent No.: US 7,417,727 B2
(45) Date of Patent: Aug. 26, 2008

(54) METHOD AND APPARATUS FOR STANDOFF DETECTION OF LIVENESS

(75) Inventors: Leonid Polonskiy, St. Louis, MO (US); Jeffry Golden, Creve Coeur, MO (US); Clinton Boyd, St. Peters, MO (US); Arie Kaplan, University City, MO (US); Lawrence Hanebrink, Chesterfield, MO (US); Qingzhong (James) Cai, Plano, TX (US); Andrew Cilia, McKinney, TX (US)

(73) Assignee: Clean Earth Technologies, LLC

( * ) Notice: Subject to any disclaimer, the term of this patent is extended or adjusted under 35 U.S.C. 154(b) by 127 days.

(21) Appl. No.: 11/296,804

(22) Filed: Dec. 7, 2005

(65) Prior Publication Data

US 2007/0268485 A1 Nov. 22, 2007

Related U.S. Application Data

(60) Provisional application No. 60/633,861, filed on Dec. 7, 2004.

(51) Int. Cl.
*G01J 3/00* (2006.01)

(52) U.S. Cl. .......................... 356/300; 356/51; 356/419; 382/115

(58) Field of Classification Search .......... 356/300, 356/71, 317, 52, 51, 419; 382/124, 115; 600/407, 473, 475, 476, 477
See application file for complete search history.

(56) References Cited

U.S. PATENT DOCUMENTS

| 2004/0153284 A1 | 8/2004 | Bernstein et al. |
| 2004/0240712 A1* | 12/2004 | Rowe et al. |
| 2005/0162647 A1* | 7/2005 | Okumara et al. |

OTHER PUBLICATIONS

Attas et al., Visualization of cutaneous hemoglobin oxygenation and skin hydration using near-infrared spectroscopic imaging, 2001, Skin Research and technology, 7: 238-245.*

(Continued)

*Primary Examiner*—F. L. Evans
*Assistant Examiner*—Abdullahi Nur
(74) *Attorney, Agent, or Firm*—Kang Intellectual Property Law, LLC; Grant D. Kang

(57) ABSTRACT

A method for remotely detecting whether a subject is alive, comprising the steps of determining a calibration spectral signature for light reflectance from living skin, normalizing the calibration spectral signature values to the calibration reflectance value at a reference wavelength, storing the normalized calibration spectral signature, determining a subject spectral signature of the light reflectance of a region of skin of the subject whose liveness is to be determined, normalizing the subject spectral signature values to the subject reflectance value at the reference wavelength, comparing the normalized subject spectral signature with the normalized calibration spectral signature for at least one wavelength, generating a subject liveness signal based on the comparison of the normalized subject spectral signature with the normalized calibration spectral signature, and emitting the subject liveness signal.

35 Claims, 22 Drawing Sheets

OTHER PUBLICATIONS

Jacquez, J., et al., "Spectral Reflectance of Human Skin in the Region 0.7-2.6", 1955, vol. 8, pp. 297-299.

Angelopoulou, E., "The Reflectance Spectrum of Human Skin", 1999, Technical Report MS-CIS-99-29, pp. 1-14.

Sheard, C., et al., "The Color of the Skin as Analyzed by Spectrophotometic Methods", 1929, pp. 559-613.

Pavlidis, I, et al., "Monitoring of Periorbital Blood Flow Rate Through Thermal Image Analysis and Its Application to Polygraph Testing", 2001, IEEE.

Kohlenberg, E. et al., "Determining intestinal viability by near infrared spectroscopy: A veterinary application", Vibrational Spectroscopy, vol. 38, 2005, pgs. 223-228.

Attas, M, et al., "Visualization of cutaneous hemoglobin oxygenation and skin hydration using near-infrared spectroscopic imaging", Skin Research and Technology, vol. 7., 2001, pgs. 238-245.

PCT International Search Report for PCT/US2005/044648.

* cited by examiner

METHOD AND APPARATUS FOR STANDOFF DETECTION OF LIVENESS

CROSS-REFERENCE TO RELATED APPLICATIONS

This application claims the benefit of U.S. Provisional Application No. 60/633,861 filed Dec. 7, 2004.

GOVERNMENT INTERESTS

This invention was made with government support under Contract Number DAAD05-03-C-0028 under the Counterterrorism Intelligence, Surveillance Reconnaissance System (CT-ISR) program, and thus the government has certain rights in the invention.

FIELD OF THE INVENTION

This invention relates to a method and apparatus for the detection of live people and the discrimination between live and dead persons, i.e., liveness detection, and in particular to said method and apparatus, the determination of liveness of a still person at a remote location, such determination being useful in search and rescue operations and in tactical battlefield operations.

BACKGROUND OF THE INVENTION

Currently, human liveness detection can be done by the non-invasive measurement of blood flow in a body. The methods are based on the well known Doppler effect—change of the wave frequency after reflection from a moving object. In practice ultrasonic, optical, or radar waves are used. In the case of ultrasonic or optical waves, after penetration into human skin the wave is scattered by static tissue as well as by movement of cells in blood vessels (platelets and others). While the former will stay unchanged compared to the source, the latter will be shifted in the frequency by a value proportional to the speed of scattering blood cells. As a result the scattered wave will have a broader spectrum and this effect can be measured and converted into the blood flow speed. Much of the prior art uses Doppler blood flow measurement methods and apparatus. Some of the methods use ultrasonic waves and some use laser radiation. Still other prior art uses Doppler radar measurement or detection of a beating heart or body part motion that is associated with breathing, i.e., respiration. In the Doppler radar case, a radar pulse is transmitted, and scatters from a breathing body or penetrates the body and scatters off a beating heart or moving body parts such as lungs and chest cavity, which move in the course of breathing, and the Doppler frequency shift of the reflected signal is sensed or measured. Additionally, some prior art employs thermal sensing of body temperature as an indication of liveness. One method of such thermal sensing is the detection of long wave infrared emission by a warm body.

As blood flow, breathing, and a beating heart exist only in live subjects the above methods can be in principle used for liveness detection. However, direct application of the known non-radar methods and apparatus to human liveness detection in combat or rescue operations is not feasible for several reasons. Ultrasonic Doppler velocimetry works only in proximity of a subject, preferably requiring contact between a transducer and a detector with the body, because the signal gets reduced dramatically with increased the distance from the body. The laser Doppler measurements do not require contact, but are still limited in distance. In addition, the laser source has a recognizable signature and can be detected by the enemy, which is not acceptable for covert operations. Also, for Doppler measurements a laser with very narrowband radiation must be used, as the speed of blood cells is slow and high precision measurement is necessary. Such a laser adds significantly to the cost and weight of the instrument. Pulse Doppler radar measurements are used in combat and emergency situations, but they are active measurements as they employ electromagnetic emissions that scatter from the subject. As such, the fraction of emitted power that is returned to the sensor is proportional to the inverse fourth power of the distance, i.e., the range, between the transmitter and the subject. As a consequence, such liveness detection requires substantial emitted power or energy and comprises a significant signature that can be detected by an enemy or if the power is reduced, then significant limitations in range result.

There are many multi-spectral and hyperspectral sensors and methods for a variety of physiological measurements, but these sensors and methods rely on close proximity or contact with tissue for such measurements. Such sensors and monitors are cumbersome and not well suited for remote sensing. Sensors that use long wave infrared detection of body temperature are not reliable when ambient temperature is near body temperature. At extreme temperatures, heat flow models must be used to account for the departure of skin temperature from normal body temperature. As a result, such sensing may be unreliable, require cumbersome calibration, or be useful only in limited conditions of ambient temperature and wind. Further, such sensors typically have poor spatial resolution and so rely on close proximity.

The ability to remotely determine if a wounded soldier was alive or dead would be of substantial benefit to battlefield leaders who must decide whether to risk personnel in recovering a soldier who might already be dead and thus unfortunately beyond medical help no matter how fast that help is provided.

The determination of liveness would also be useful to assess whether a still person poses a threat or to detect persons who are difficult to detect visually because they are in a visually cluttered scene or partially concealed. The detection and classification of pixels in a scene that correspond to live skin or tissue are useful for the detection of the use of cosmetics, i.e., 'make-up', prostheses, masks, or other means of concealment or alteration of appearance or disguise. With other indication of liveness such as locomotion or Doppler sensing of blood flow, breathing, or heartbeat, the identification of skin or tissue as not live would indicate an altered appearance that may be part of a disguise.

SUMMARY OF THE INVENTION

In view of the limitations now present in the prior art, the present invention provides a method and device for Standoff Liveness Detection, which has a significant range of operation. In addition, the method does not require a laser source and can be passive, i.e. it can use ambient illumination. For this reason an instrument based on this method cannot be detected during operation.

Our approach to distinguishing between live and dead subjects is based on the difference between spectral reflectance of live and dead humans and animals. Living skin and tissue are supplied with oxygenated hemoglobin, while dead skin and tissue are not. Moreover, the water content, and consequently the optical characteristics, are also different for live and dead skin or tissue. As a result the spectral signatures are quite different between live and dead. The difference can be remotely detected by an observer using a viewing apparatus.

The apparatus for implementing the proposed method includes an optical viewer with spectral analysis capabilities. When the observer looks at a subject through the viewer and positions the viewer so that the central circle is locked on a face or another bare skin area, a spectral signature of this skin area is acquired by the apparatus and compared with the spectral signature of living human skin stored in memory. If the signatures are the same, then the apparatus so indicates to the observer, who is then informed that the subject is alive, and if the signatures are different, the apparatus indicates that the subject is nonliving material. In a similar manner, the viewer may be a multi-spectral or hyperspectral imaging device with spectral analysis capabilities, which perform the comparison of observed spectral signature with the signature of living skin stored in memory. Instead of or in addition to viewing skin with its water content and the oxygenated hemoglobin in the dermis, the method may be used in the sensing of tissue to determine liveness provided that such living tissue is supplied with oxygenated hemoglobin such as is the case with the conjunctiva of the eye, which is a vascular tissue. It is also the case with the hypodermis, epithelial tissue, and other parts of the body having significant blood perfusion or oxygenated hemoglobin content.

Therefore, in one aspect the invention is a method for remotely detecting whether a subject is alive, comprising the steps of determining a calibration spectral signature for light reflectance from living skin, normalizing the calibration spectral signature values to the calibration reflectance value at a reference wavelength, storing the normalized calibration spectral signature, determining a subject spectral signature of the light reflectance of a region of skin of the subject whose liveness is to be determined, normalizing the subject spectral signature values to the subject reflectance value at the reference wavelength, comparing the normalized subject spectral signature with the normalized calibration spectral signature for at least one wavelength, generating a subject liveness signal based on the comparison of the normalized subject spectral signature with the normalized calibration spectral signature, and emitting the subject liveness signal.

In another aspect the invention is an apparatus for remotely detecting whether a subject is alive, comprising a viewer and an analyzer. The viewer comprises an objective and a beamsplitter which together form a first intermediate image and a second intermediate image; a reticle placed in the plane of the first intermediate image; an eyepiece for viewing the first intermediate image through the reticle; an optical fiber bundle comprising a plurality of sub-bundles, a first end of the optical fiber bundle being disposed in the plane of the second intermediate image such that the plurality of sub-bundles splits a central region of the second intermediate image into a plurality of light signals; and a sensor comprising at least one photodiode assembly, wherein at least one optical fiber sub-bundle is optically coupled to the photodiode assembly. The analyzer comprises: a digital signal processor and a memory, such that the digital signal processor generates a liveness signal if a normalized subject spectral signature is substantially equivalent to a normalized calibration spectral signature template stored in the memory and otherwise generates a not live signal.

In yet another aspect the invention is an apparatus for remotely detecting whether a subject is alive, comprising a hyperspectral imaging system comprising at least one camera for collecting a plurality of subject images formed by photons reflected from the subject, each image representing photons having wavelengths within a sub-portion of the electromagnetic spectrum; an image processor comprising memory for storing a reference spectral signature image, and logic circuits for comparison of the subject images to the reference spectral signature image to determine whether the subject is alive; and an output device to indicate whether the subject is alive.

In still another aspect the invention is a method for remotely detecting whether a subject is alive, comprising the steps of determining a calibration spectral signature for light reflectance from living skin; storing the calibration spectral signature; determining a subject spectral signature of the light reflectance of the subject whose liveness is to be determined, wherein the subject spectral signature is collected as an image comprising a plurality of pixels; comparing the subject spectral signature with the calibration spectral signature; generating a subject liveness signal for each pixel of the image, based on the comparison of the subject spectral signature for each pixel with the calibration spectral signature; and displaying the subject liveness signal.

BRIEF DESCRIPTION OF THE DRAWINGS

FIG. 14A shows the exterior and the interior of the device is shown in FIG. 14B.

FIG. 17A, is detected in the same image, FIG. 17B.

DETAILED DESCRIPTION OF THE INVENTION

Figure 1:
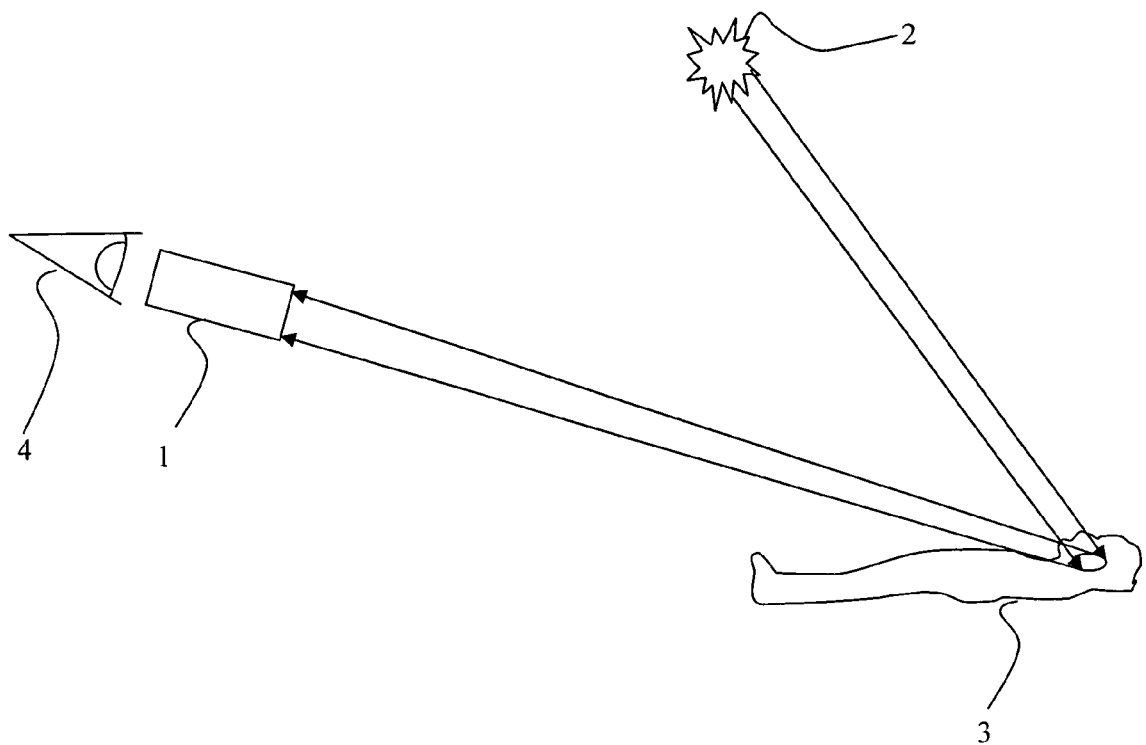
FIG. 1 is a schematic diagram of a method for standoff human liveness detection in accordance with the principles of this invention.

A method for standoff detection of human liveness is illustrated schematically in FIG. 1. It is based on the difference between spectral skin or tissue reflectance of live and dead humans. The difference can be detected remotely by an observer using either a non-imaging viewer or an imaging apparatus. To implement the method an optical viewer with spectral analysis capabilities 1 is used by an observer 4 to locate a subject 3, who is illuminated with a light source 2. The optical viewer compares the spectral signature of the subject with the spectral signature of living human skin or tissue prerecorded into its memory. If these two signatures are similar, the optical viewer generates a signal for the observer to let him know that the subject is alive. If the signatures are different then the signal that indicates liveness is not generated, which means the subject is dead. In another embodiment the viewer generates a signal that indicates that a live subject is not viewed. Generating a signal to indicate a lack of living material within the optical viewing field is preferred since this indicates that an analysis has been completed and distinguishes from a situation where the machine might malfunction, for example due to power failure.

The methods of the present invention can also be used to automatically detect whether a subject is wearing a disguise or other potential suspicious conditions. When used in conjunction with another biometric indication of liveness, such as locomotion (e.g. the subject is observed to move under his own power), body temperature, or Doppler sensing of blood flow, breathing, or heartbeat, the detection and classification of liveness or the lack thereof for skin or tissue, which is expected to be live, are an indication of altered appearance. Such alteration of appearance can be indicative of cosmetics, prostheses, masks, or other means of disguise or abnormal condition. Therefore, if for a particular subject there is obtained an initial indication of liveness using a motion-, heat-, or appearance-based biometric indicator such as those discussed herein, this information can then be compared to the results of spectral-based liveness indicators to determine whether the subject's exposed skin, e.g. on the subject's face, is in fact living tissue. If a subject is determined to be alive by motion-, heat-, or appearance-based biometric indicators but the subject's exposed skin is determined by spectral methods not to be living tissue, then it may be concluded that the subject is wearing a disguise or prosthetic device and may thereby warrant further surveillance.

The light source can be natural (sun) or artificial (flood light, for example). In any case it should be broadband enough to permit recording a multi-spectral image in the range sufficient for liveness detection. This can be explained by the graphs shown in FIG. 2. The solid curve depicts the spectral reflectance (spectral signature) of living human skin, while the dashed curve corresponds to the spectral signature of dead human skin. The difference is associated with subcutaneous blood flow of oxygenated hemoglobin transported from lungs to all parts of the body. Obviously, a dead person does not have blood flow and there is no oxygenated hemoglobin in the skin tissue, consequently the spectral signature becomes almost flat in the visible range of the spectrum. The proposed method includes the relative measurement of the skin spectral reflectance at several wavelengths. Using relative values is important as objects/subjects in a scene can be illuminated differently and can have variable brightness. The ratio of intensities in the selected spectral bands should stay nevertheless constant.

Figure 3:
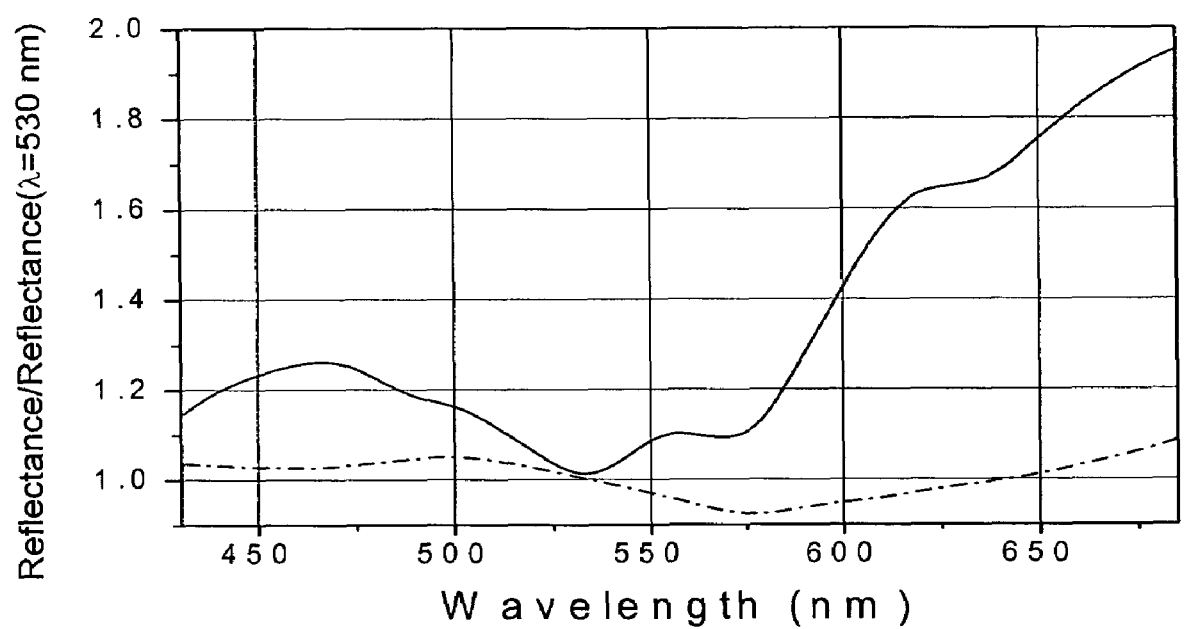
FIG. 3 shows spectral signatures of living (solid line) and dead (dashed line) human skins normalized to their values at $\lambda=530$ nm.

For example, the wavelength $\lambda_0=530$ nm can be selected as the reference point, because spectral reflectance of living skin has a minimum value in this point. If we normalize the reflectance values of each curve to its reflectance at the reference wavelength $R(\lambda_0=530$ nm$)$, we will get the graphs shown in FIG. 3. It depicts the ratios of reflectivities in all spectral bands to the reflectivity at the reference wavelength 530 nm. It can be easily seen that the ratio (or normalized reflectance $R_{norm}$) is almost constant in the visible spectral range for dead skin $R_{norm}=1\pm0.1$, while for living skin it changes in a significantly broader range $1<R_{norm}<1.95$.

Figure 4:
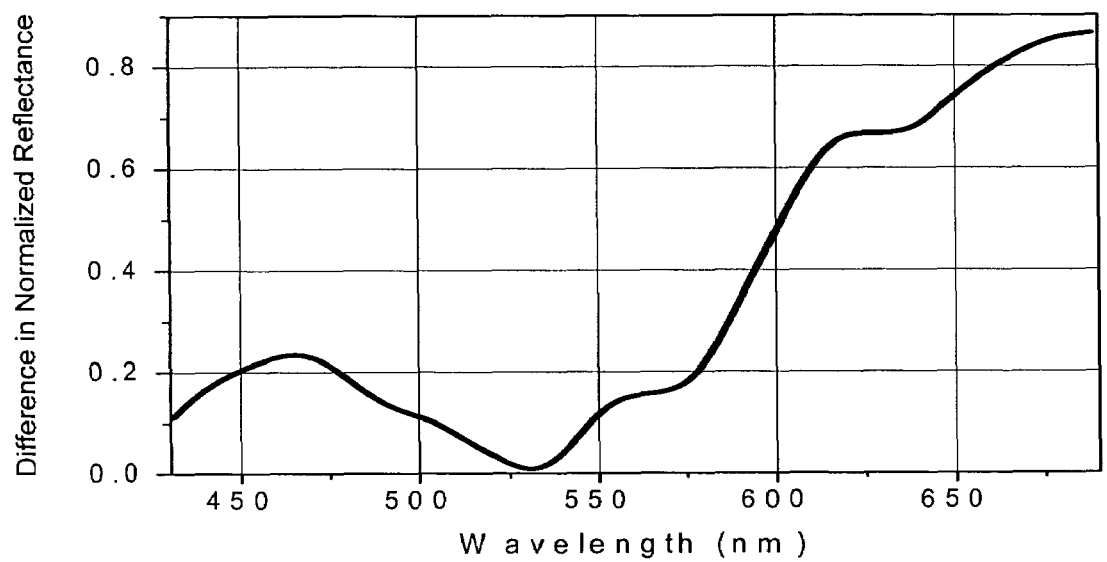
FIG. 4 shows the difference between the normalized signatures for the living and dead skins.

FIG. 4 shows the difference between normalized reflectance for living and dead skin. The wavelengths corresponding to the largest difference between the normalized reflectance of dead and live skins are the best for liveness detection. From FIG. 4 it is easy to conclude that these wavelengths are in the blue (450-480 nm) and red (600-700 nm) ranges of the spectrum when the reference point is selected at 530 nm. Based on the above discussion the optimum detection wavelengths can be selected. Therefore, in a preferred embodiment a liveness determination is made by comparing the normalized reflectance from skin or other vascularized tissue from a test subject to similarly normalized reflectance values obtained from a calibration subject. Normalized reflectance values are determined by calculating the ratio of the reflectance measured at one or more wavelengths from a reflectance spectral signature, preferably in the ranges of 450-480 nm and 600-700 nm, to a reference wavelength, preferably 530 nm. In general the reference wavelength is preferably chosen from a region of the spectrum wherein the reflectance values are most similar between live and dead skin, whereas the wavelengths used for assessing liveness are preferably chosen from regions of the spectrum having the greatest difference in reflectance between live and dead skin. The calibration spectral signature is collected from a known live sample or several known live samples, preferably in the field under the same conditions (e.g. lighting) as those used for collecting the test spectral signature. However, in other embodiments the calibration spectral signature is collected at a different time and/or location and is stored in memory for later use. If the ratio determined from the test spectral signature is comparable to the ratio calculated from the calibration spectral signature, then a liveness indication signal is generated. For high accuracy, i.e., a low error rate, many samples from several live subjects can be acquired to determine a distribution of ratio values that correspond to a live subject. The minimum values for liveness, i.e., the "live limit minimum" then can be specified as a percentile of the distribution. If several ratios form the data set for a given observed sample, then the criterion for liveness can be selected as a specified minimum number of data points in the data set having values above the "live limit minimum". The several ratios may be a relatively narrow range of wavelength, e.g., 500 nm-650 nm, or it may span a much larger range.

Figure 5:
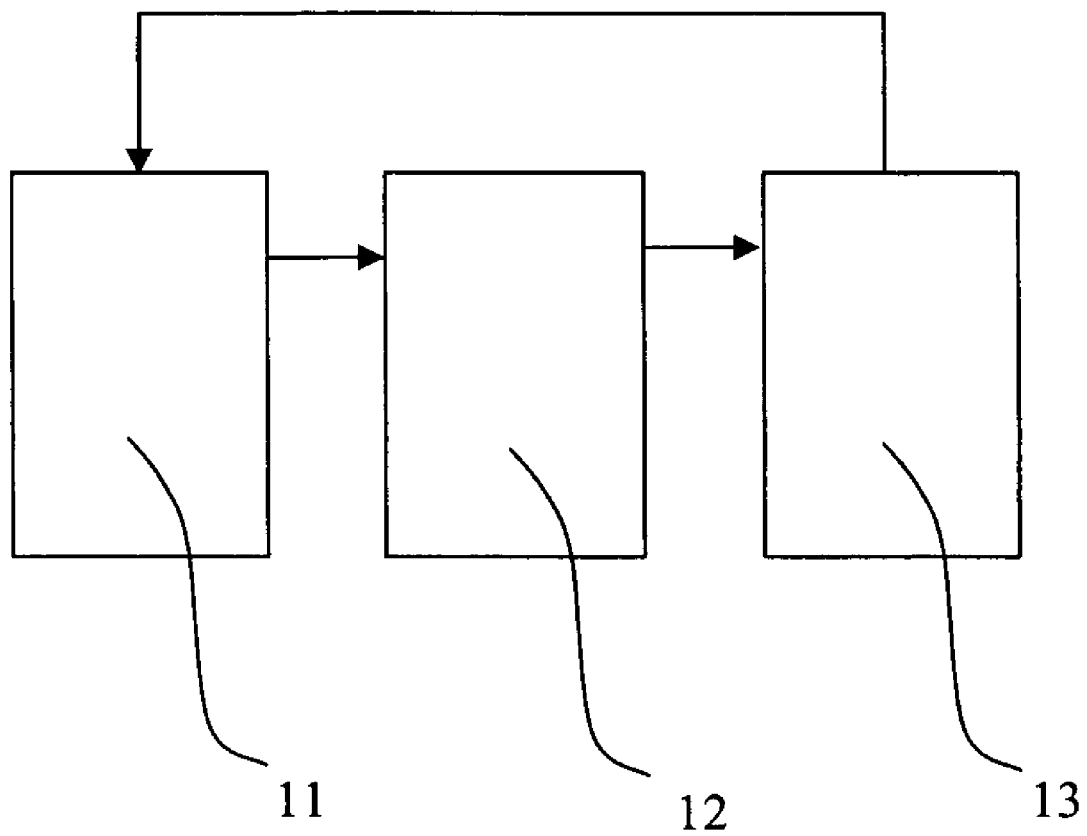
FIG. 5 is a schematic of the proposed apparatus for the standoff human liveness detection.

The block diagram of the apparatus for implementing the proposed method is shown in FIG. 5. It comprises three modules: a viewer 11, a sensor 12, and an analyzer 13. The viewer is a modified binocular, a rifle scope, a telescope or any other optical device capable of imaging remote objects with magnification. It is operated by an observer, who positions the viewer so that the central circle is locked on a face or another bare skin area of a subject under investigation. The light flux corresponding to the encircled spot goes to the sensor 12, where its spectral intensities at several wavelengths, optimized to liveness detection according to FIG. 4 data, are measured. The reflectance data is transferred to the analyzer 13, which normalizes the reflectance and compares it with the values corresponding to living human skin and stored inside the analyzer. If a coincidence is detected, the analyzer sends a signal visible to an observer to indicate that the subject is alive. If a discrepancy is detected, no signal is sent, by which the observer is informed that the subject is nonliving material. The viewer may also send a visible signal if no coincidence is detected that indicates the subject is dead and informs the observer.

Figure 6:
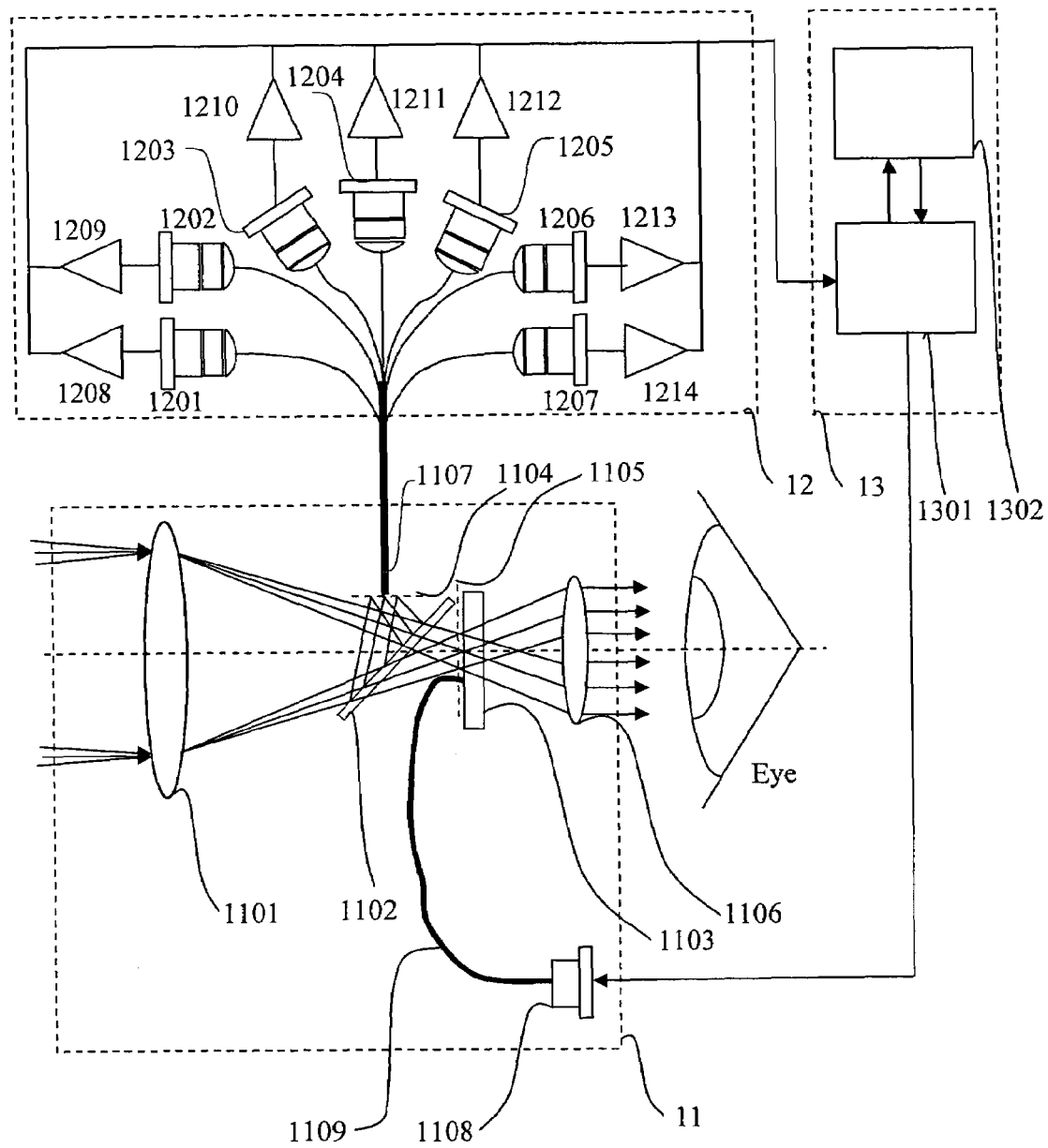
FIG. 6 is a block-diagram of the arrangement for applying the method to the standoff liveness detection of humans.

A detailed diagram of all three modules: a viewer, a sensor, and an analyzer, is shown in FIG. 6. The viewer 11 includes an objective 1101 and beamsplitter 1102, creating together two intermediate images 1104 and 1105 of a scene, a reticle 1103, placed in the plane of the first intermediate image 1105, a multi-track fiber bundle 1107 with an input tip in the plane of the second intermediate image 1104, one or more light emitting diodes 1108, and one or more fibers 1109. The reticle 1103 has superimposed on it a circle 1111 which is optically conjugated, or aligned, with the end of the fiber bundle 1107 so that whatever the operator places to be viewed within the circle 1111 will be what is collected by the fiber bundle 1107, transmitted to the photodiodes, and analyzed by the system for a liveness determination.

The sensor comprises several photodiode assemblies 1201-1207 and the same amount of preamplifiers 1208-1214 for improving the sensitivity of the photodiodes and signal to noise ratio of the device.

The analyzer consists of a digital signal processor (DSP) 1301 and a memory chip 1302.

Figure 7:
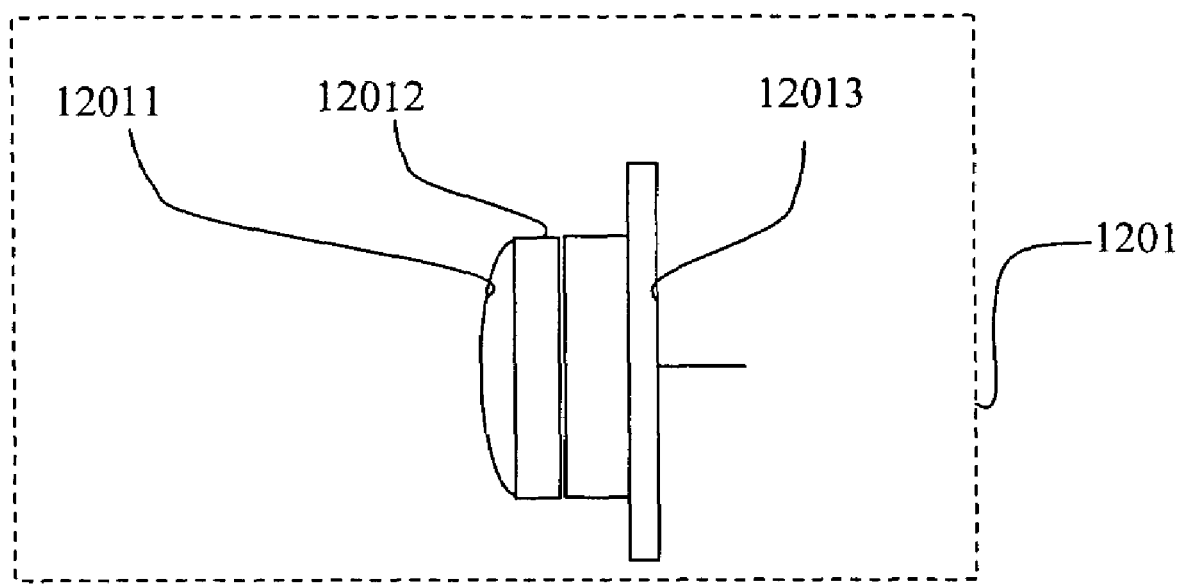
FIG. 7 is one of several photodiode assemblies in the sensor module.
Figure 8:
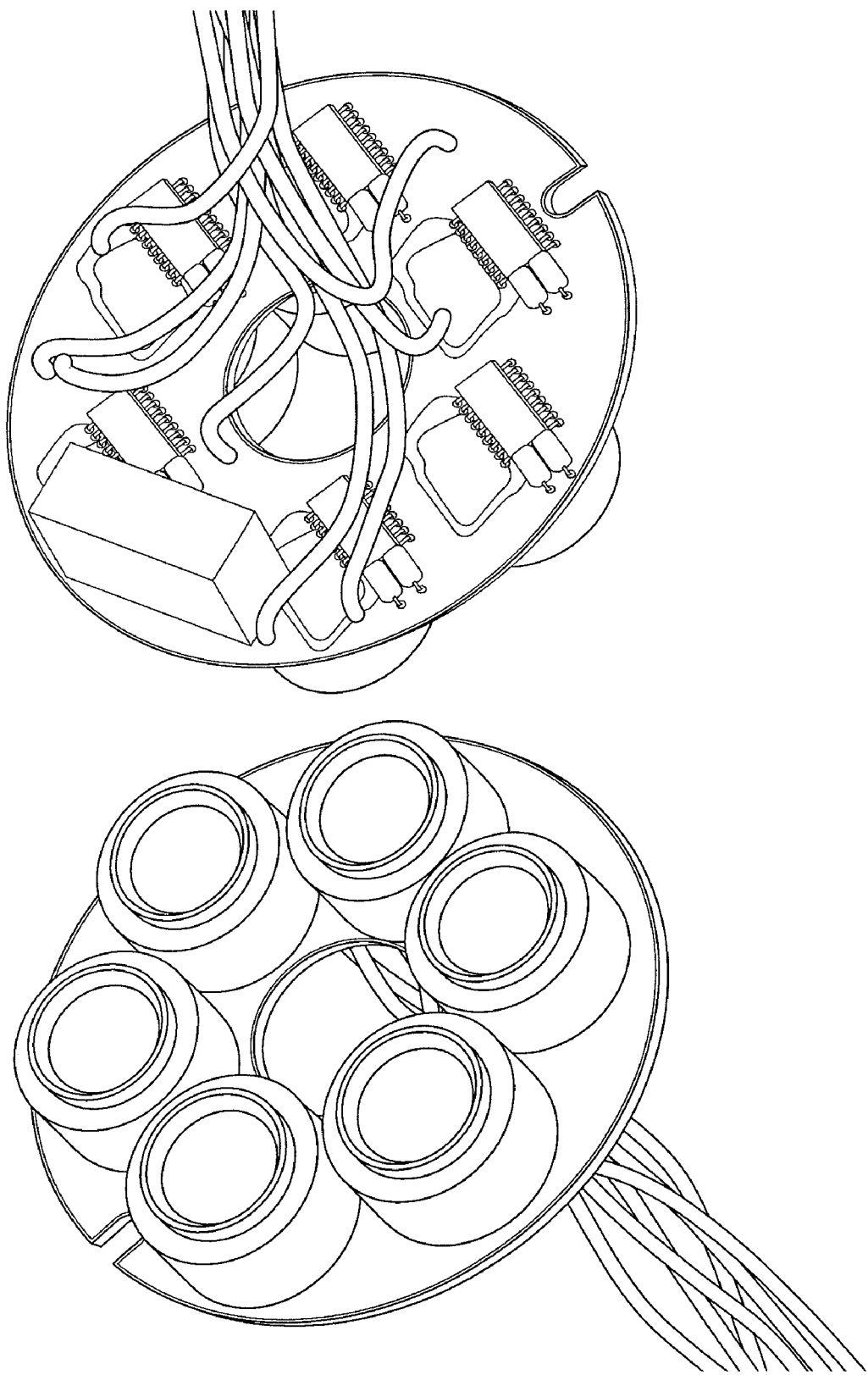
FIG. 8 Multi-spectral detectors (l) and processor (r) liveness monitor.

Each photodiode assembly includes a lens 12011, an optical bandpass filter 12012, and a photodiode 12013, as shown for photodiode assembly 1201 in FIG. 7. The bandpass filters all are for different wavelengths, which are selected in the spectral ranges, corresponding to those preferred for distinguishing between living and dead human skin: blue (450-480 nm) and red (600-700 nm), as it has been discussed above. A working embodiment of the sensor is shown in FIG. 8.

Figure 9A:
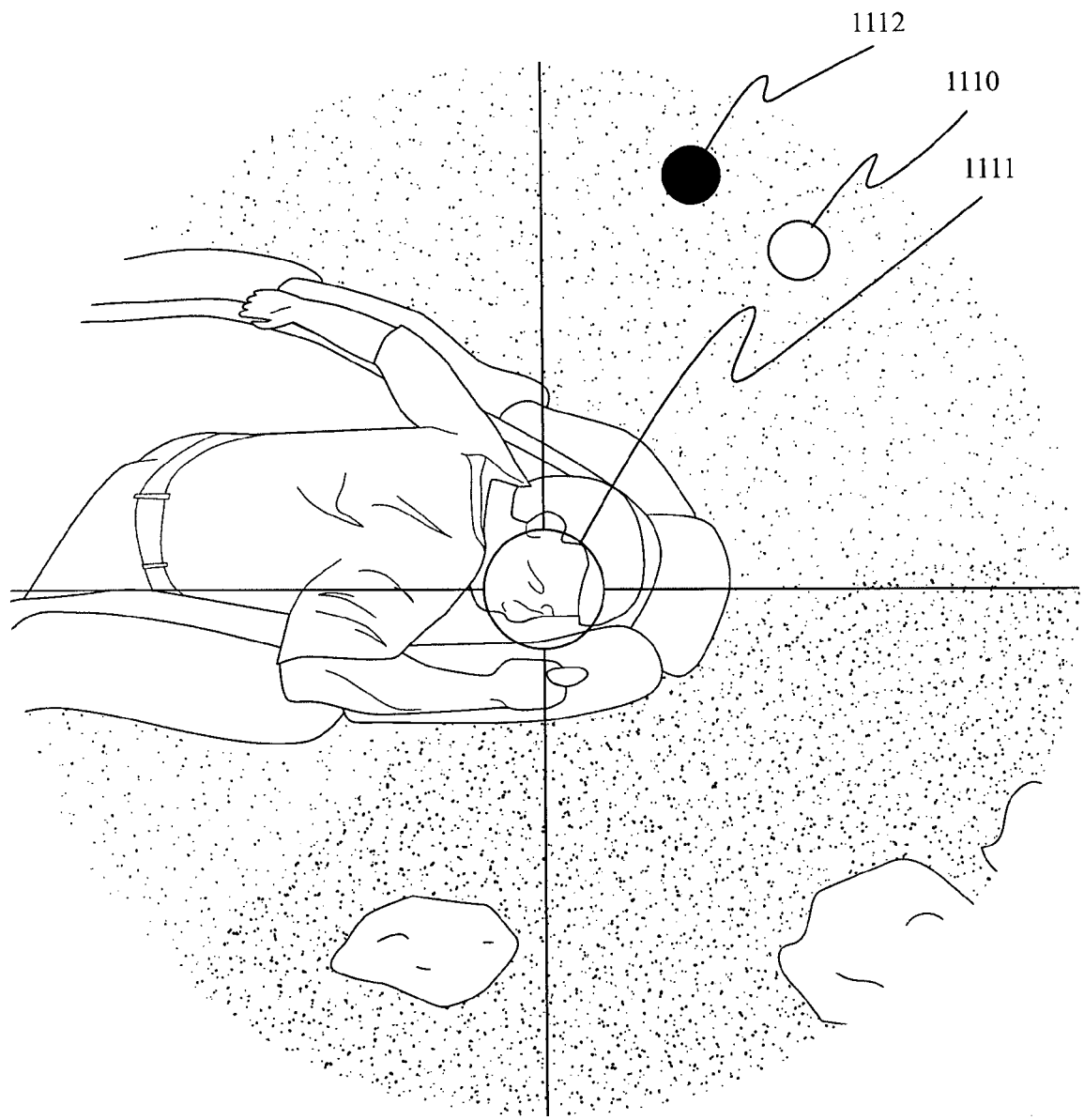
FIG. 9 is a field of view of the standoff liveness detector.
Figure 9B:
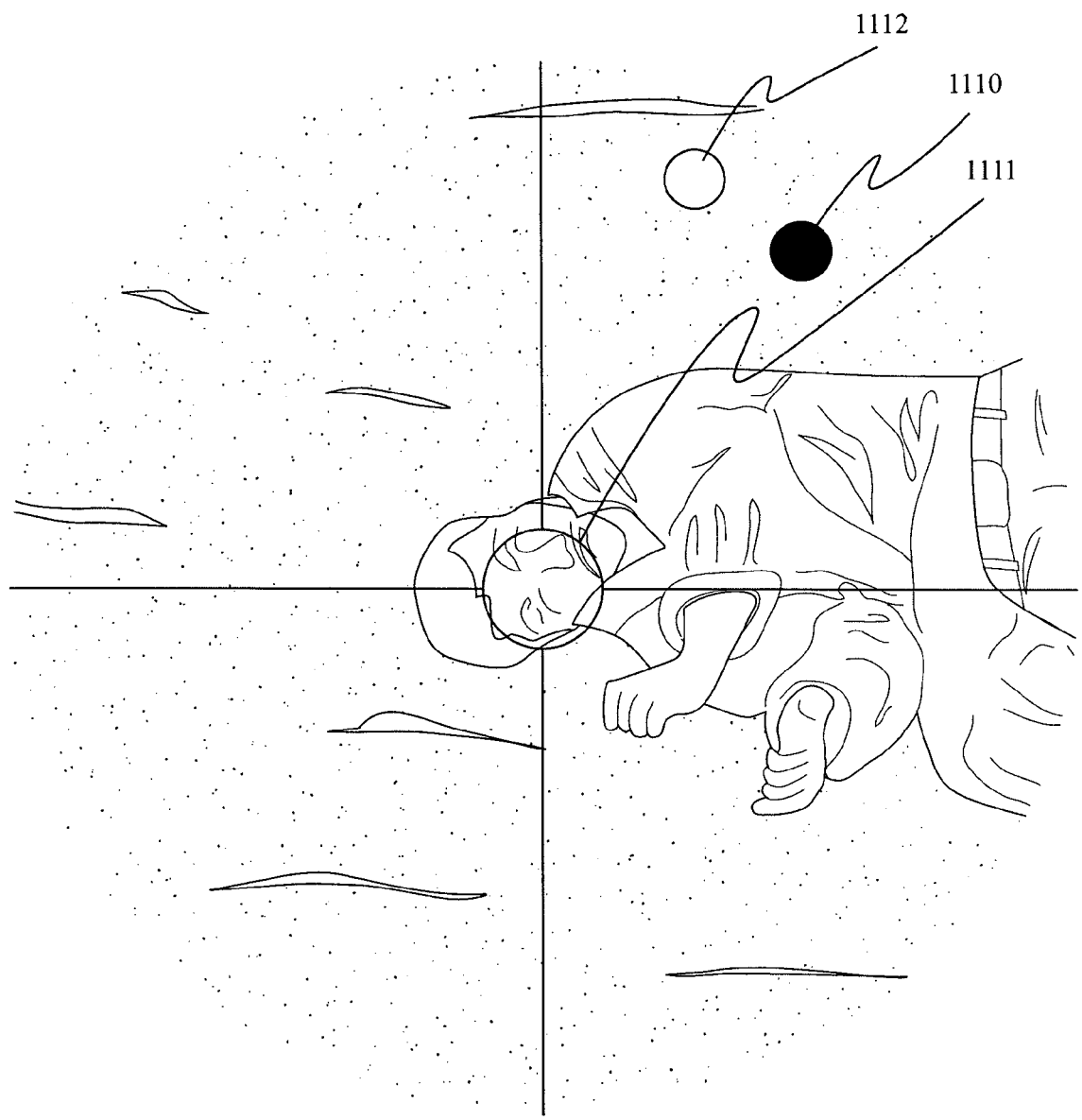

As it can be seen from FIG. 9, the observer field of view includes a central circle 1111 (the pattern is on the reticle 1103, FIG. 6) and a liveness indicator (the end of the fiber 1109, coupling the LED 1108 to the reticle 1103, FIG. 6). A second fiber 1109, coupling a second LED 1108 to reticle 1103 may be used as a 'not-live' indicator in addition to the liveness indicator.

According to this embodiment the proposed Standoff Liveness Detector works as follows:

1. An observer calibrates the Standoff Liveness Detector by acquiring the spectral signature of a live subject.

1.1 The Standoff Liveness Detector has to be positioned so that the central circle 1111 is on the skin of a live person—FIG. 7. After that the observer initiates calibration by pressing a button. If there is no live subject available the observer can use his/her hand as a calibration object.

1.2 The image of the calibration object/subject is projected by the objective 1101 on the plane of the intermediate image 1105. The beamsplitter 1102 splits the light beam into two perpendicular sub-beams and the second intermediate image 1104 is formed. To increase the sensitivity of the Detector the beamsplitter optionally can transmit only spectral band(s) not used for detection (for example, blue-green-yellow spectral ranges 500-540 nm). In this case all photons corresponding to those spectral bands preferred for detection will be reflected to form the second intermediate image 1104.

1.3 The multi-track fiber bundle 1107 used in the apparatus has a single input tip with random distribution of fibers (non-coherent bundle) and multiple output tracks. It accepts the light flux concentrated inside the central circle 1111 on the reticle 1103, splits the light between multiple output tips, and guides it to all photodiode assemblies 1201-1207. The number of output tracks is equal to the number of the photodiodes deployed in the Sensor, while the spatial distribution of the fibers in the input edge is random (the fibers are not mapped to specific output faces—i.e. a non-coherent fiber bundle is used). The latter provides mixing of the light signal from the central circle and uniform splitting in equal averaged fractions for coupling through the fiber bundle to each photodiode rather than mapping of different parts of the object/subject to the individual photodiodes.

1.4 Light in each photodiode assembly is focused by lens 12011 through optical bandpass filter 12012 to the sensitive area of photodiode 12013. Therefore, only light in the selected spectral band, determined by the optical bandpass filter parameters, is measured by each photodiode.

1.5 After amplification by the preamplifiers 1208-1214 the electrical signal proportional to the light flux in the given spectral band gets acquired and processed by DSP 1301.

1.6 The results of the measurement (normalized spectral signature of the living skin) are sent to the memory 1302 and stored there for future use as a template.

2. The observer determines the liveness of a remotely located subject.

2.1 The observer watches a scene with his/her eye(s) through the viewer module of the Standoff Liveness Detector and finds a remotely located subject whose liveness has to be determined. He positions the viewer so that a bare skin area of the subject occupies the central circle in the field of view (FIG. 7) and acquires the spectral signature of the subject by pressing a button.

2.2 The same processes as described in paragraphs 1.3-1.5 occur.

2.3. The acquired data is compared with the template by the DSP. If the data sets are close to each other the DSP generates an electrical signal driving the LED 1108, which in turn generates light. The light is transported through the fiber 1109 to the reticle 1103. The facet of the fiber 1109 serves as the indicator of liveness 1110 in the field of view—FIG. 7. The observer can see in the same field of view that the liveness detector is on and the person is alive. If the spectral signature of the subject is different than the template stored in the memory, the liveness-indicating LED remains dark as well as the liveness detector.

3. The observer repeats operation 2 for all subjects in the scene who lie still but may be alive.

In another embodiment, a second LED and fiber are used to indicate 'not-live' if the criteria for the DSP to generate a 'liveness' signal are not met. In this case, the DSP generates an electrical signal driving a second LED 1108, which in turn generates light, which may be of a color different from the liveness indicating LED, and the light is transported by a second fiber 1109 to reticle 1103 so that the facet of the second fiber 1109 serves as an indicator of 'not-live' 1110 in the field of view.

Figure 10:
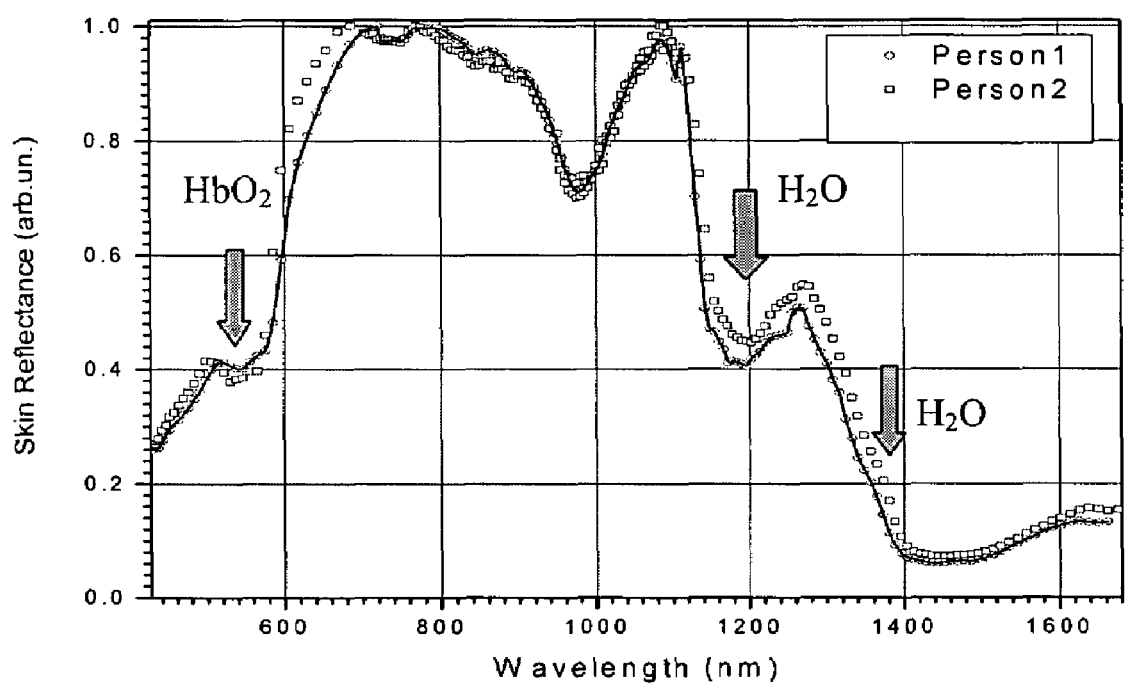
FIG. 10 Typical human hyperspectral signatures from the visible to SWIR wavelengths. The colored arrows indicate very distinct features in the signatures due water and or hemoglobin.

In yet another embodiment, the liveness detector may take the form of a hyperspectral imaging (HSI) sensor. Hyperspectral imaging is a pixel by pixel measurement, which is made as the continuous division in wavelength of a broad band (typically optical) signal. That is, the reflectance intensity at each of a series of closely neighboring wavelengths, or narrow, contiguous bands of wavelengths or piecewise contiguous bands of wavelengths is measured for each pixel in an image. Thus for each pixel in the image the technique produces a continuous plot of reflectance within the measured region of the spectrum (FIG. 10). Hyperspectral imaging is a well established approach that has been used in many different technical areas including medicine, remote sensing, counter mine applications and earth monitoring. By looking at the relative amounts of the reflectance signal at each wavelength (or small bands of wavelengths) separately, it is possible to extract much more information than can be obtained from a signal that is the sum of the reflectance across many wavelengths or integrated across a broad band of wavelengths. Peaks and troughs in the hyperspectral signature can often be correlated with known absorption or emission bands and thus be used to identify constituents of the volume through which the data was taken e.g. the presence of oxy-hemoglobin or de-oxyhemoglobin or water. This is shown in FIG. 10. In FIG. 10 the hyperspectral reflectance signature was obtained from two living human subjects in the range of 400 nm to 1700 nm at regular, contiguous bands. The skin reflectance spectra in both cases show distinct features corresponding to absorption due to water ($H_2O$) or oxygenated hemoglobin ($HbO_2$). Among other requirements, collecting hyperspectral reflectance images requires a means for filtering the incoming light destined for the camera detector so that each image represents the reflectance within a narrow range of wavelengths, for example 20 nm wide bands.

Figure 11:
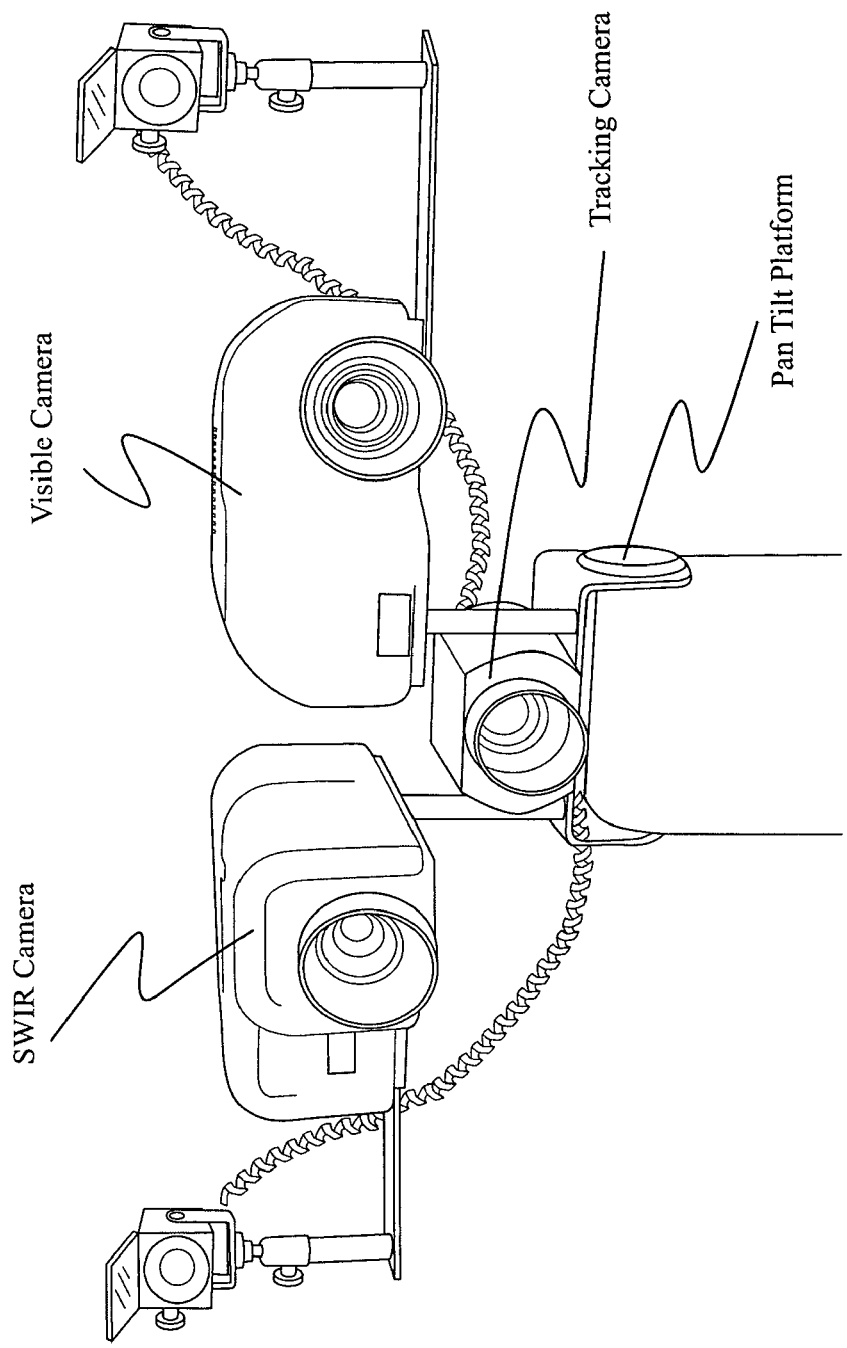
FIG. 11 Hyperspectral Imaging Human Detector Sensor

We have built a hyperspectral human detection sensor (FIG. 11) that can automatically detect the presence of a human from long ranges (200 m or further). The sensor (known and trademarked as SpectraSentry) uses up to 3 cameras (visible, NIR and SWIR) to span the range from 400 nm to approximately 1700 nm, although human detection can typically be performed using a single SWIR camera operating in the 1000 nm to 1600 nm range. The sensor works by obtaining the hyperspectral signature from any exposed human skin (FIG. 11) e.g. hands, face, head, neck etc. and comparing it to standard data representing an "average" human. The comparison between current and average or typical data is performed using one or more algorithms developed by the inventors and detailed in the next section. The "average" human data is obtained by collecting images cubes (i.e. hyperspectral signatures) from a large number of people and averaging the results.

Figure 2:
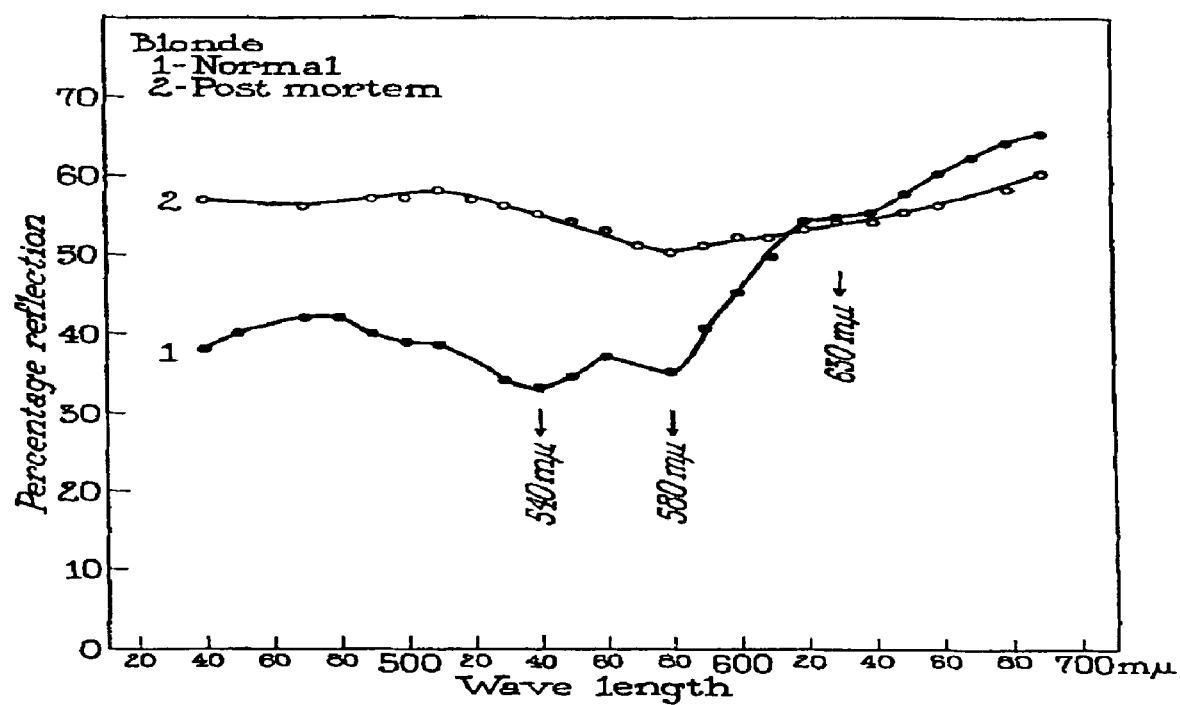
FIG. 2 is a graph of the spectral signatures of living and dead human skins.

Since death can be associated with lack of oxygen in the blood, and as the hyperspectral signature of human skin depends quite significantly on hemoglobin and in particular, the amount of oxygen in the hemoglobin, the CET implementation of HSI is an excellent approach to use to determine if the object being imaged is alive or dead (FIG. 2). In addition to being used to determine if a person is dead or live, this approach can be used to detect the use of prostheses, cosmetics, masks, or other means of disguise for defeating, confusing, or 'spoofing' of biometric based access systems such as finger print readers and, to a lesser extent, iris scanners, by confirming that the body part that is offered to the biometric device is in fact living tissue.

The algorithm that is used for human detection can also be used as a liveness algorithm. Since a typical human hyperspectral signature is known a priori, a digitally stored signature can be obtained prior to the measurement for comparison with the signal from the person for whom liveness is to be determined. The simplest approach is on a pixel by pixel basis, to look at the distance in a least squares sense between the measured data and the "typical" human signature. That is, the spectral signature of a particular pixel in the subject image is compared with the spectral signature of an "average" human (determined as described above). If the measured and predetermined "average" human spectral signatures are close enough (below the threshold), then that pixel is called human and may be marked in the image, e.g., it may be colored red, or some other unambiguous marking may be used. If the two spectral signatures are far apart (above the threshold), then that pixel is called non-human and in one embodiment is marked in a different color, say black. Typically, for a particular embodiment of a viewer or imaging system, the threshold can be determined empirically by measurement of a number of persons $N_c$ who are representative of the target population and then selecting a threshold value that captures a specific fraction $f_c$ of the live data distribution. The probable error rate can be determined by well known statistical methods that are based on the values of $N_c$ and $f_c$.

Other methods of determining if a pixel should be classified as human or non-human include the spectral angle mapper (SAM) and the use of a neural network. The spectral angle mapper measures spectral similarity by finding the angle between the spectral signatures of two pixels. Since it uses only the "direction" of the signatures and not their "length", the SAM is insensitive to frequency-dependent variations in the scene illumination.

Figure 12A:
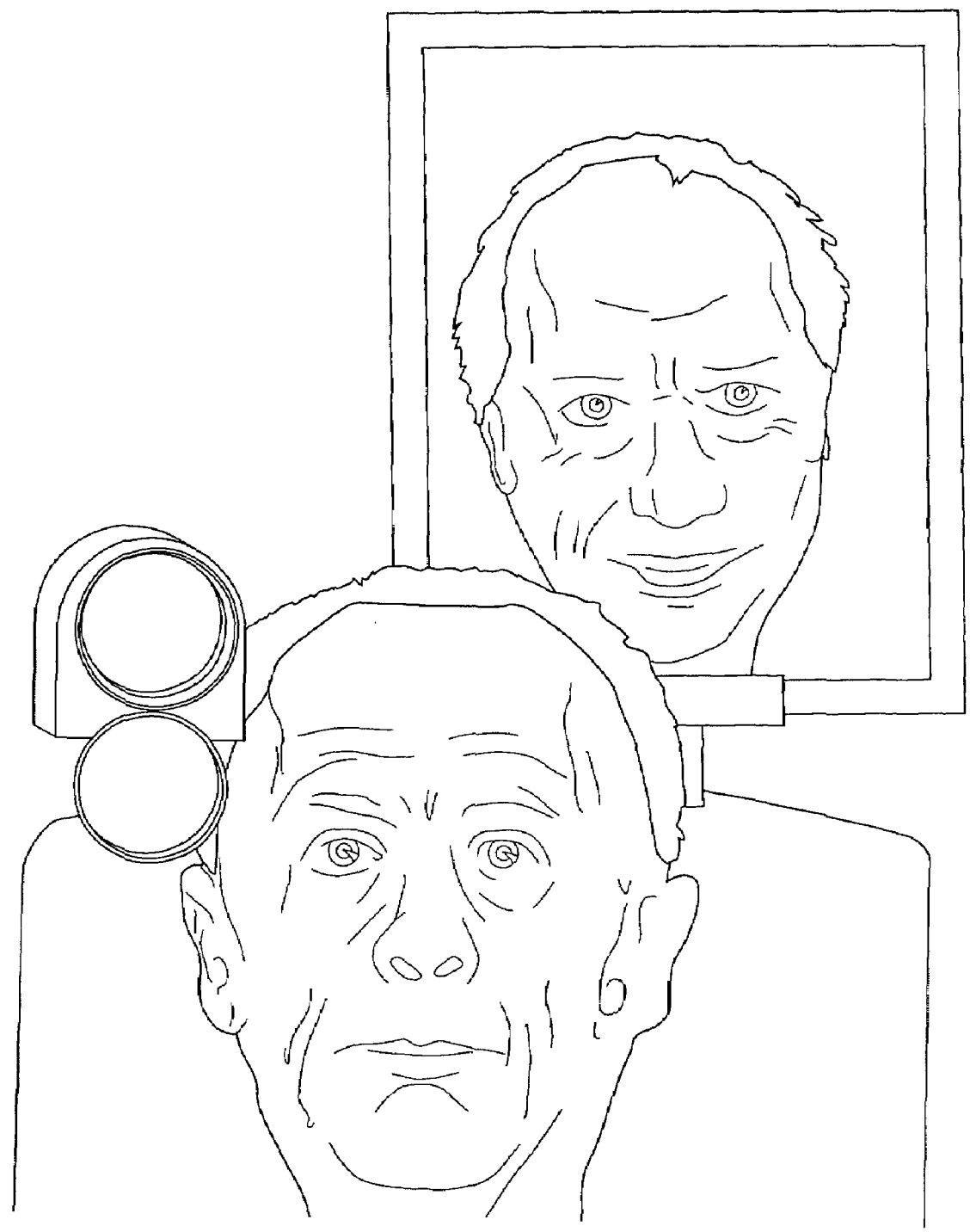
FIG. 12A Test scene using a human face and a picture of the same person.
Figure 12B:
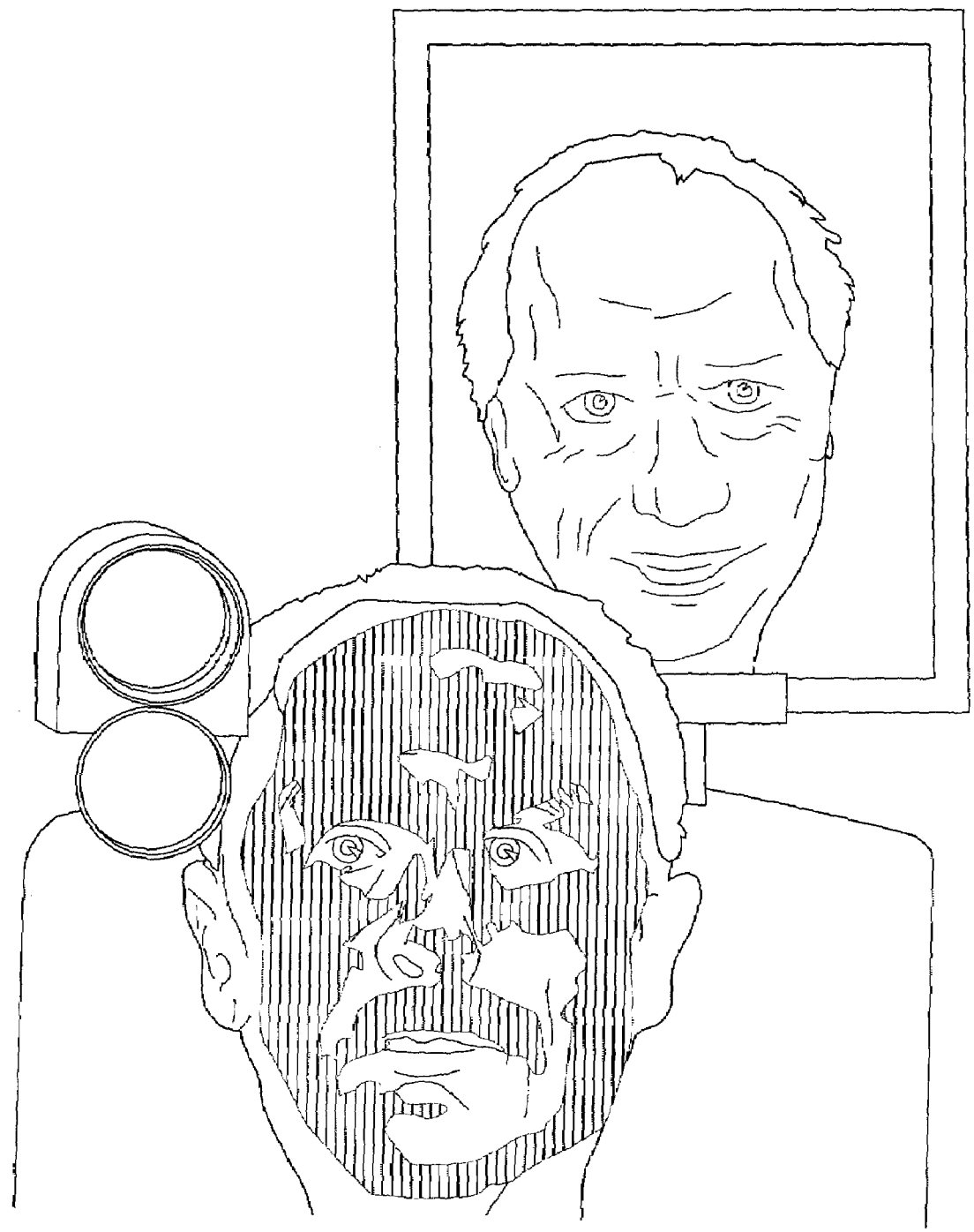
FIG. 12B Human detection based on Euclidean distance.
Figure 12C:
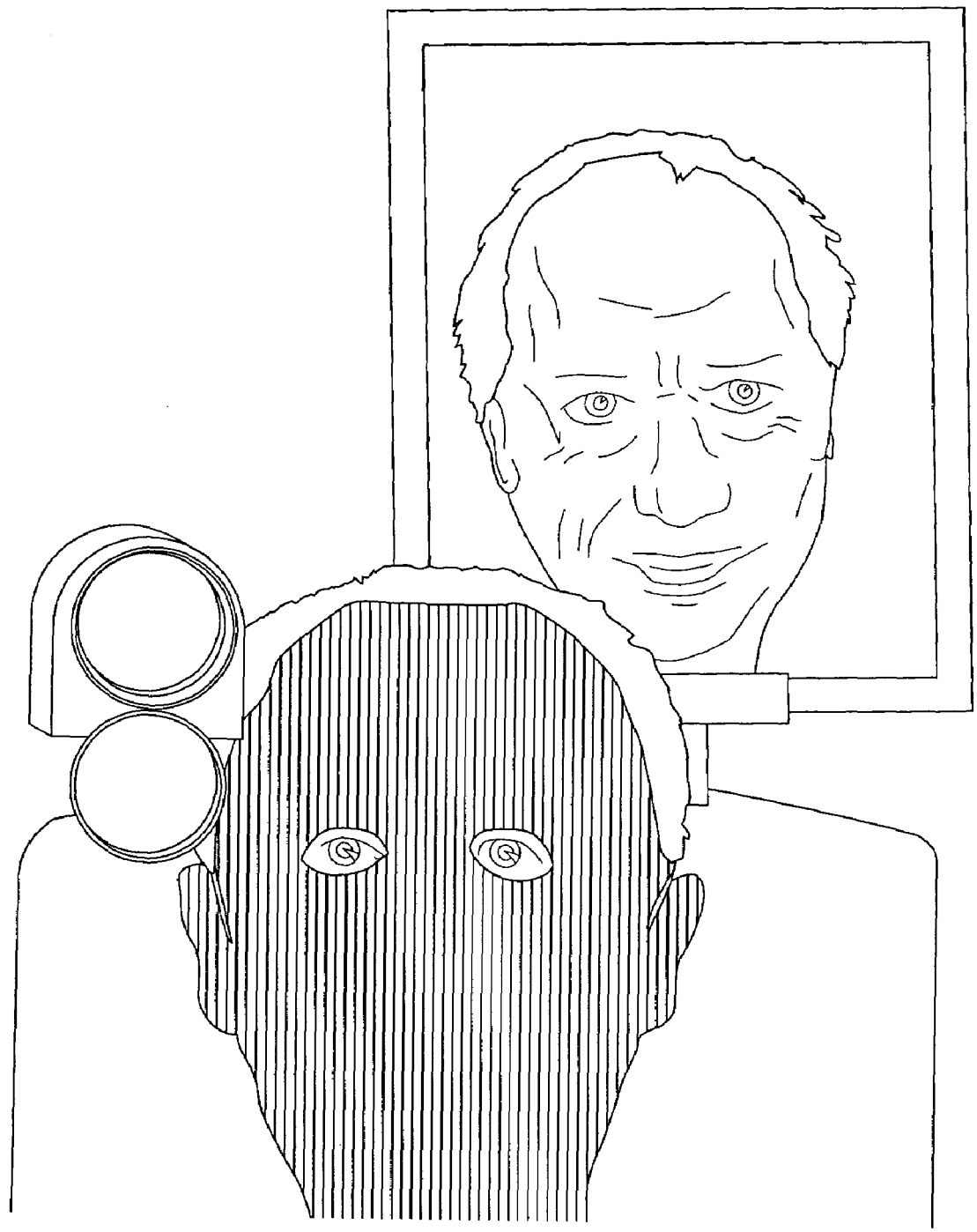
FIG. 12C Human detection using a 3-layer neural network

In another embodiment, a multi-layer perceptron (MLP) feed-forward neural network is used to improve detection accuracy at the expense, however, of needing initial training. Typical 'live' human detection results are shown in FIGS. 12a-12c. In FIG. 12a, the test scene is shown, which contains the face of a live person and a picture of the same person. In FIG. 12B, the pixels are classified according to a Euclidian spectral distance measurement, i.e. least squares, with those pixels determined to be from a 'live' person colored in red (shown as vertical hatching in FIG. 12B). In FIG. 12C, the classification is based on a 3-layer neural net algorithm, again with the 'live' person pixels indicated in red (shown as vertical hatching in FIG. 12C). Superior performance is seen in FIG. 12C as the contiguous pixels corresponding to the 'live' person's face and ears.

Spectral Angle Mapper (SAM) is an automated method for comparing image spectra to individual spectra or a spectral library (Kruse, F. A., Lefkoff, A. B., Boardman, J. W., Heidebrecht, K. B., Shapiro, A. T., Barloon, J. P., and Goetz, A. F. H., The spectral image processing system (SIPS)—Interactive visualization and analysis of imaging spectrometer data: *Remote Sensing of Environment*, v. 44, p. 145-163 (1993)). The algorithm determines the similarity between two spectra by calculating the "spectral angle" between them, treating them as vectors in a space with dimensionality equal to the number of bands N. Graphically, this may be depicted as vector projections on multiple planes, for each of which the coordinate axes are reflectivities in the spectral bands i and j ($1<i, j<N+1; i\neq j$). Because only the direction of the spectral vectors is used and not their length, the method is insensitive to the unknown gain factor, and all possible illuminations are treated equally. Poorly illuminated pixels will fall closer to the origin. The material color is defined by the direction of its unit vector. The angle between the vectors is the same regardless of the length, while the latter relates only to illumination intensity. There are multiple projections of N-dimensional spectral vector, associated with each pixel, where N is the number of spectral bands. By measuring angle in the N-dimensional feature space SAM classifies all pixels as belonging or not to each given class. Spectral angles are determined for spectral vectors, corresponding to each pixel. This value is assigned to the corresponding pixel in the output SAM image, one output image for each reference spectrum. The derived spectral angle maps form a new data cube with the number of bands equal to the number of reference spectra used in the mapping. Thresholding is typically used to determine those areas that most closely match the reference spectrum. SAM calculates the angular distance between spectral vector for each pixel in the image and the reference spectra or end-members in N-dimensions. The result is a classification image showing the best SAM match at each pixel.

Artificial Neural Networks (NN) find currently broad application in hyperspectral imaging for classification and target detection. They represent a non-determinstic approach to hyperspectral classification. The advantages of NN-based approaches for classifying hyperspectral images have been recognized for a while (see, for example, J. A. Bendicktsson, P. H. Swain, O. K. Ersoy, "Neural network approaches versus statistical methods of classification of multisource remote sensing data", *IEEE Trans. Geosci. and Remote Sensing,* 28, 540 (1992)). NNs are considered to be powerful classification tools because of their nonlinear properties and the fact that they make no assumptions about the distribution of the data. This feature is useful in cases where no simple phenomenological model exists to accurately describe the underlying physical process that determines the data distribution. The NN system must be trained before use. During training an operator inserts multiple samples of various classes and allows the NN to acquire proper knowledge about a scene and objects/subjects, included in it. As the result, the NN system generates internal criteria to be used in future image classification. The NN classification is flexible and precise, but demands training and generally works slower than SAM and other deterministic algorithms.

There are some potential limitations to the liveness detection methods as described in the various embodiments above that can be overcome by practices well known in the art. One potential limitation is lack of detectability because of an insufficient number of photons reaching the sensor. The lack of received photons can be remedied by improved lighting as by the intentional illumination of the subject. This may be accomplished by one or more light sources that are situated away from the sensor. In this way, the viewer and observer may have low detectability by an enemy, while the subject is easily seen by the viewer. Improved detectability of the subject may also be obtained by use of a larger optical aperture or by longer integration time of the viewing sensor, or by use of a more sensitive optical sensor.

There are some physical limitations to the sensing that are well known and typical of optical sensing systems. These include diffraction limitations of optical systems, atmospheric attenuation, and atmospheric turbulence. The adverse effects of such phenomena can be ameliorated by means well known to those practiced in the art.

Another limitation to the method is the determination of liveness for a person or animal that is dying or has recently died, insofar as levels of oxygenated hemoglobin may remain above a liveness threshold criterion for a short period after death. During the dying process, the legal or clinical definition of death may not be precisely correlated with the determined changes in optical characteristics that are associated with levels of oxygenated hemoglobin, water content, etc. in skin or tissue. Clinical evidence has shown that levels of oxygenated hemoglobin decrease rapidly when blood flow or breathing ceases. For an adult, the loss of oxygenated hemoglobin is nearly complete within approximately 5 minutes of the cessation of breathing or heartbeat. As a consequence, the detection of liveness by the method of this invention may become uncertain or indicate not-live a few minutes after breathing or heartbeat stop although clinical or legal death may not occur for another few minutes.

Figure 13:
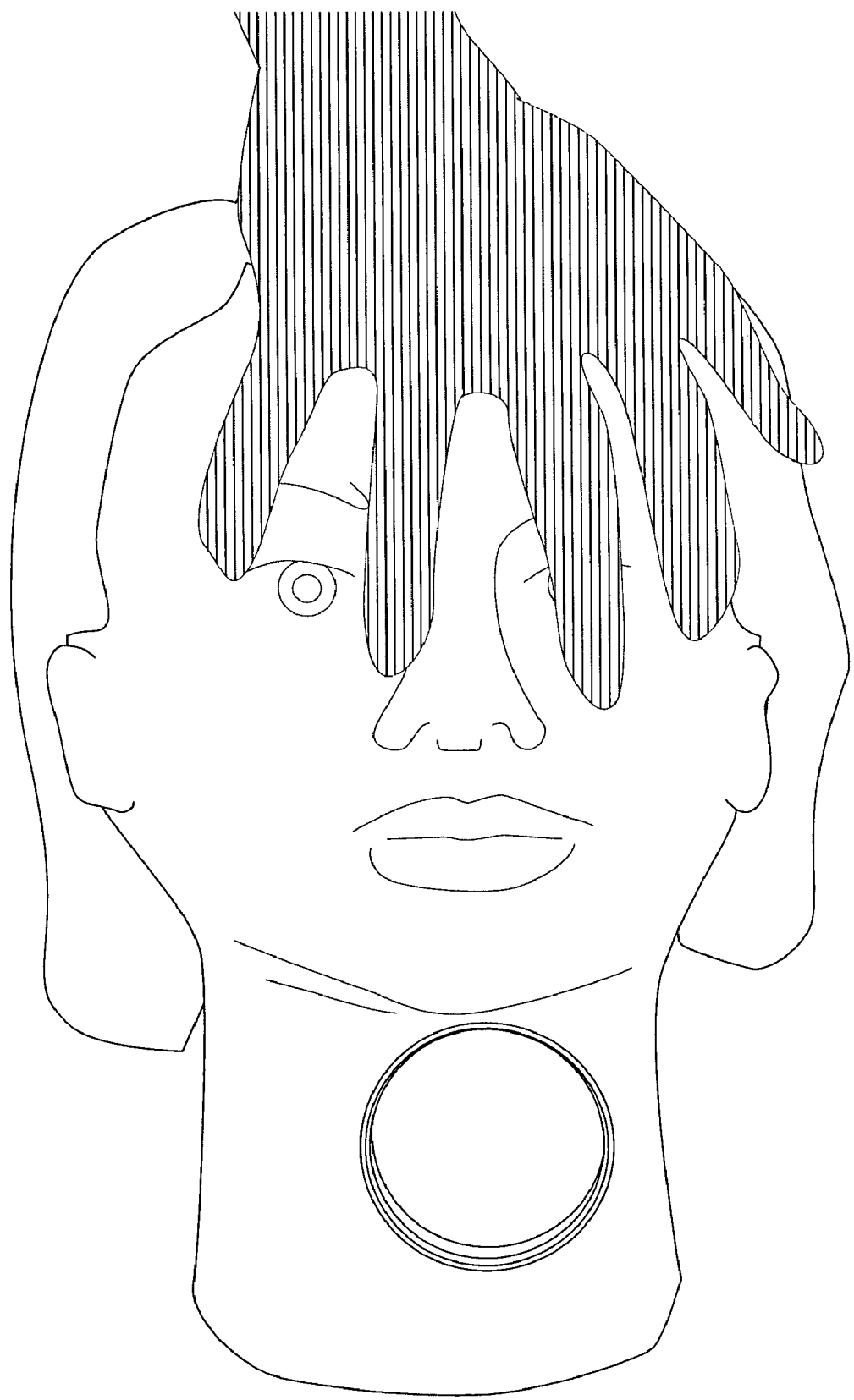
FIG. 13 Sample image from real-time continuous live human skin detection using a hyper-spectral imaging (HSI) system with an acousto-optical tunable filter (AOTF).

Laboratory tests have been performed that demonstrate the initial real-time continuous live human skin detection using a hyper-spectral imaging (HSI) system with an acousto-optical tunable filter (AOTF). (An AOTF is a solid-state electronically tunable spectral bandpass filter in which standing acoustic waves in a crystal produce index of refraction changes in the crystal, so that the crystal essentially becomes a diffraction grating with the spacing set by the distance between acoustic wave peaks.) A live human hand that is placed on the head of a manikin is shown in FIG. 13. FIG. 13 shows the results of a pixel-by-pixel HSI-based liveness determination superimposed on the image of the hand and the manikin (shown as vertical hatching in FIG. 13). FIG. 13 demonstrates that the system can discriminate between living tissue (the hand) and nonliving tissue (the manikin) which resembles living material, in that the system only determined liveness for those pixels associated with the hand and not for the pixels associated with the manikin. The system has achieved real-time (10+ frames per second) detection and can track a moving subject by using the liveness detection as the discriminant. In the example of FIG. 13, the AOTF operated in the wavelength range of 950 nm to 1700 nm, which is in the short-wave-infrared portion of the spectrum.

Figure 14A:
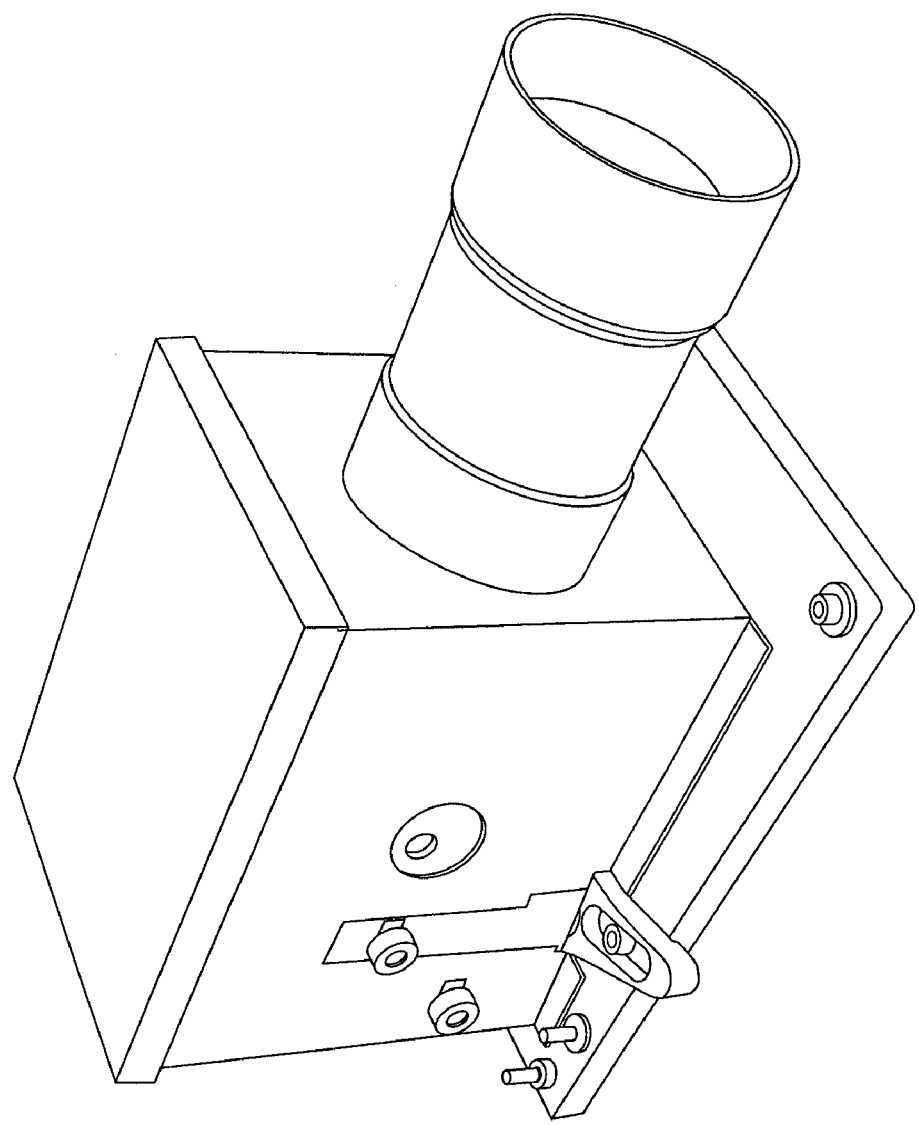
FIGS. 14A and 14B show an embodiment of the viewer for liveness detection, where
Figure 14B:
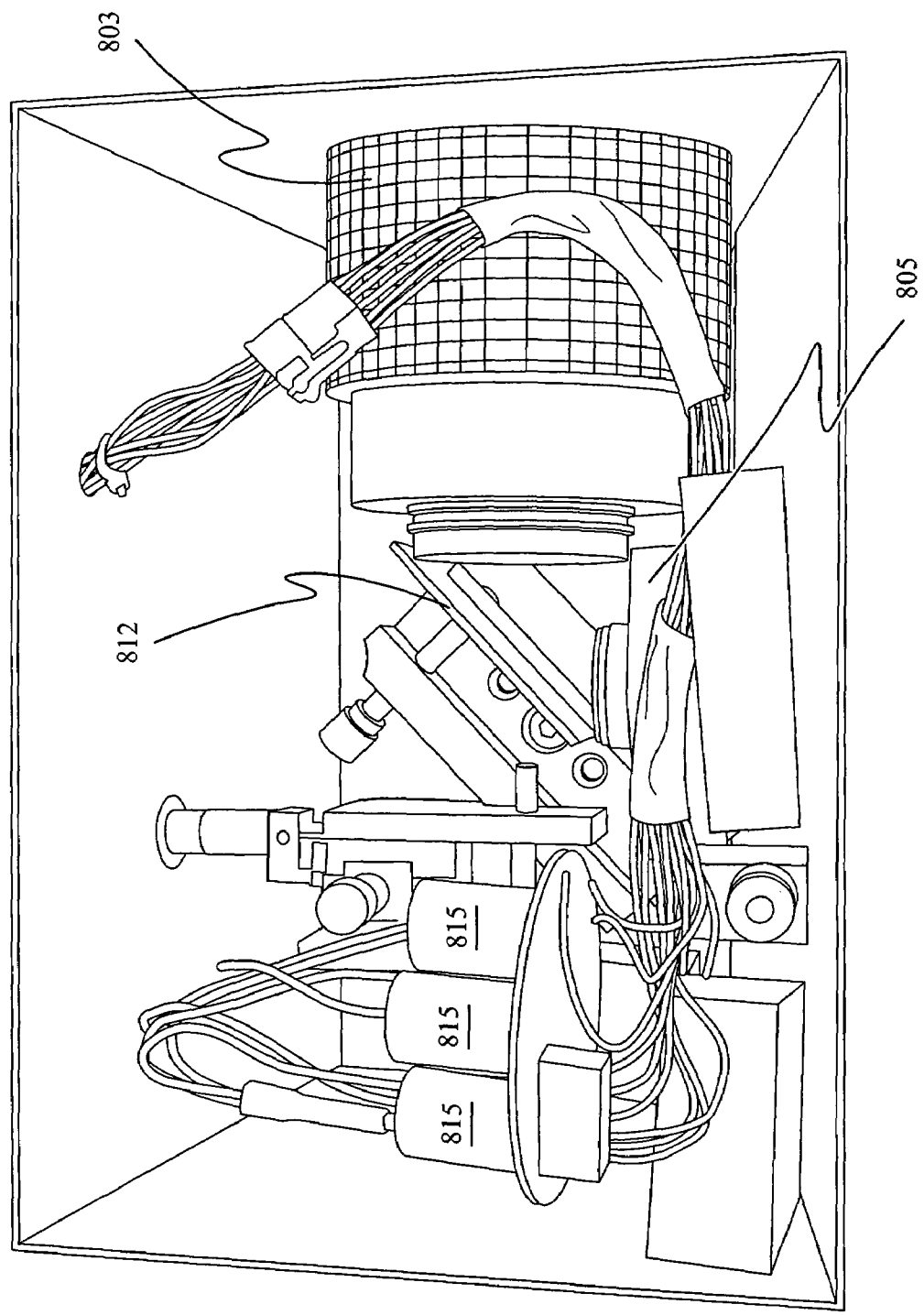

Laboratory, outdoor, and field testing have been performed with an embodiment of the viewer for liveness detection as seen in FIGS. 14A and 14B. An exterior view of the device is shown in FIG. 14A, and the interior of the device is shown in FIG. 14B. The zoom lens assembly 803 (Nikkor™ 76-180 mm, 1:4.5-5.6 D) is seen on the right. The operator views the subject through an ocular 805 with the viewing aperture on the side of the box being visible in FIG. 14A, while the ocular is seen in FIG. 14B. A beamsplitter 812 passes light to filtered detectors 815 and reflects light to the ocular 805 for observing. The viewer emits an audible sound when a live subject is viewed. The viewer is shown with the cover of its housing removed. The viewer is attached to a pan-tilt-swivel mounting for positioning when in use.

Figure 15B:
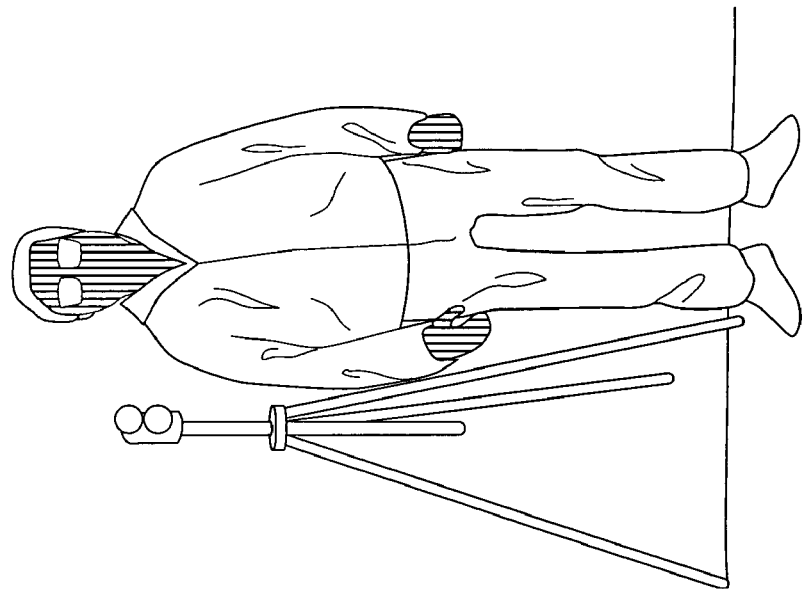
FIGS. 15A and 15B show hyperspectral human liveness detection at distances greater than 200 meters.
Figure 15A:
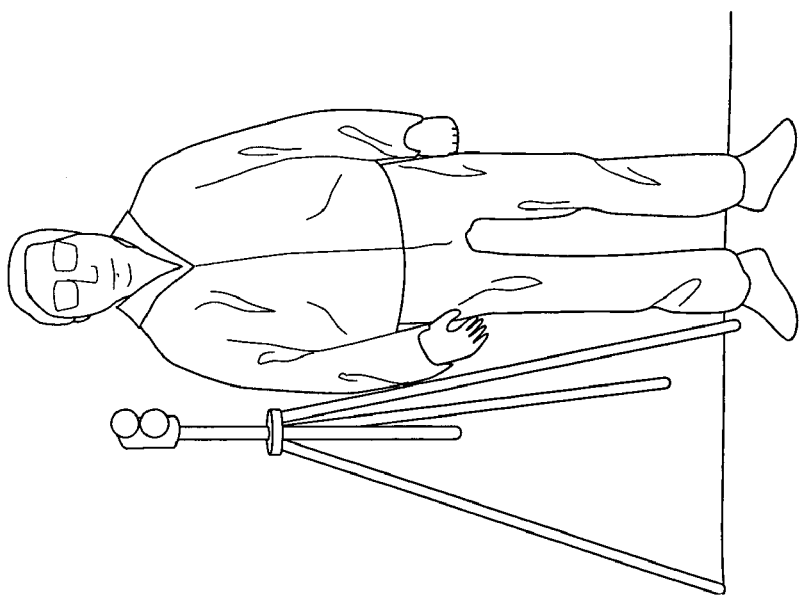

The method has also been applied to the detection of live persons (FIG. 15A) at a distance. In FIG. 15B, the face and hands of a person are identified as live at a distance of 200 m when viewed outdoors and with a line of sight that is over pavement, a pond, and turf. Pixels corresponding to liveness are sensed by the method of the invention and displayed as red colored (shown in FIG. 15B as vertically hatched portions). Using an HSI system, with a liquid crystal tunable filter (LCTF) with spectral resolution of 20 nm (that is, reflectance images are collected in successive, adjacent 20 nm wide bands of the electromagnetic spectrum), and an optical system with spatial resolution <1 mm, detection and classification of pixels with indication of live skin is performed with high accuracy. An LCTF is used to vary the wavelength of light that reaches the camera detector, so that the series of narrow, contiguous wavelength reflectance images that are required for HSI analysis can easily be collected. For the examples of FIGS. 15 and 16, a LCTF that spans the wavelength range of 420 nm to 720 nm was used.

Figure 16:
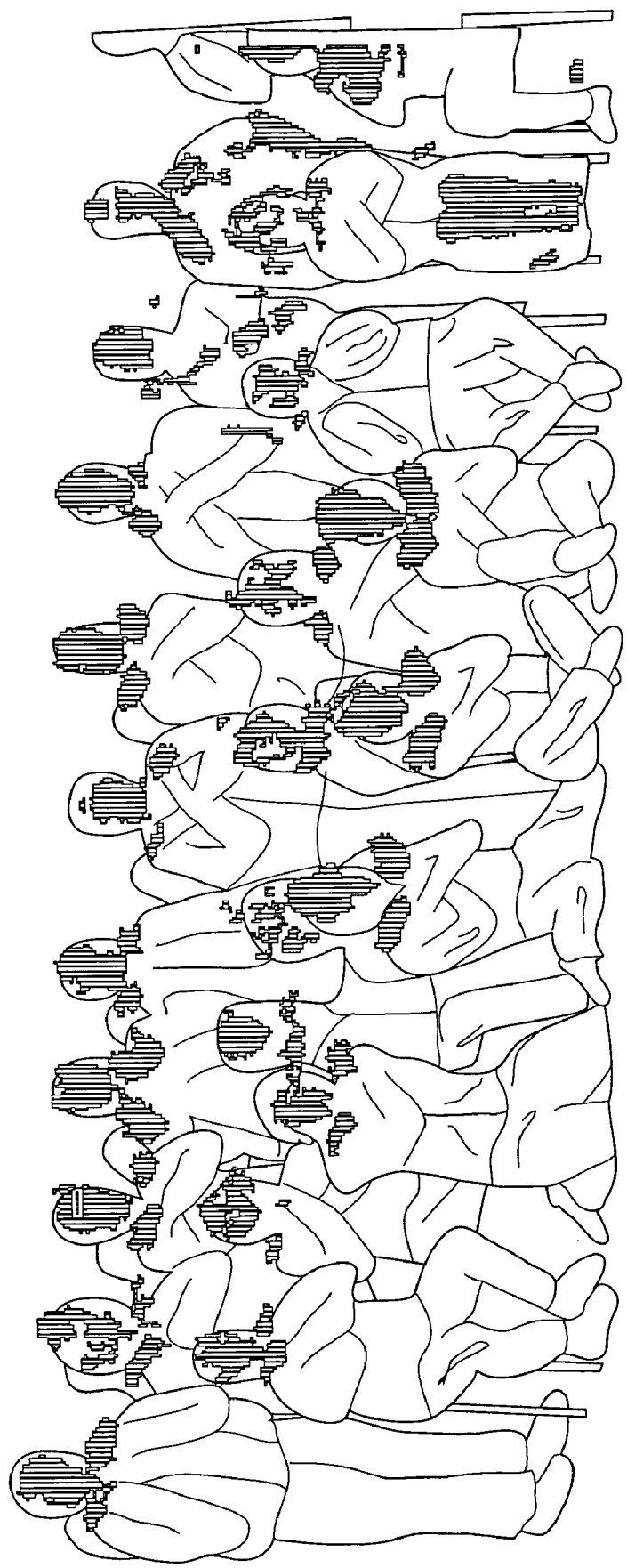
FIG. 16. The exposed skin of a crowd of live persons is detected at a range of 60 meters in an outdoor setting.

The method has also been used to identify the observable live skin of body parts of a group of persons, i.e., a 'crowd'. An analyzed image is shown in FIG. 16. Using a HSI system with LCTF, the pixels corresponding to 'live' are displayed as red colored (shown as vertical hatching in FIG. 16). With the addition of spatial analysis to further classify groups of 'live identified' pixels as specific body parts such as hands, arms, faces, heads, etc, the liveness detection can be used to aid in counting the number of individuals in a crowd.

Figure 17B:
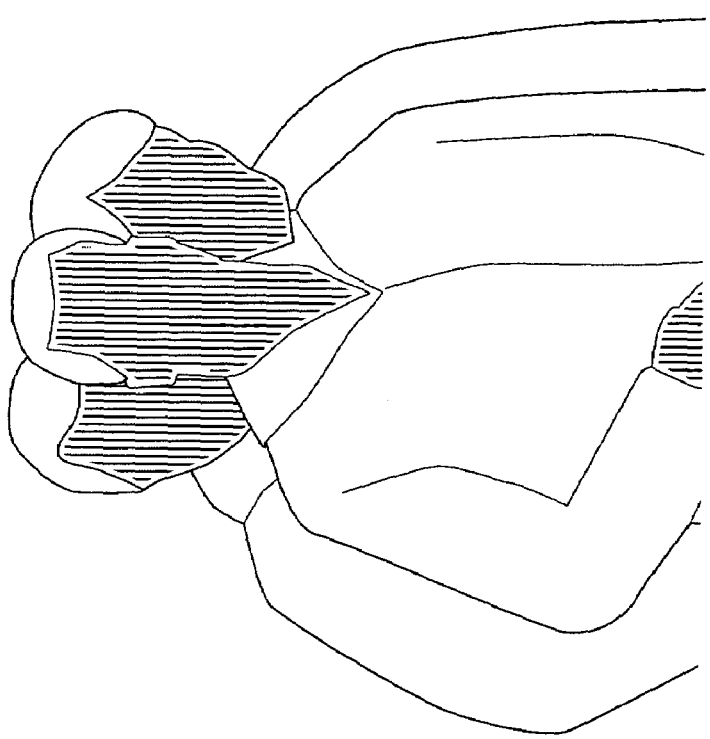
FIGS. 17A and 17B. The exposed skin of three live persons.
Figure 17A:
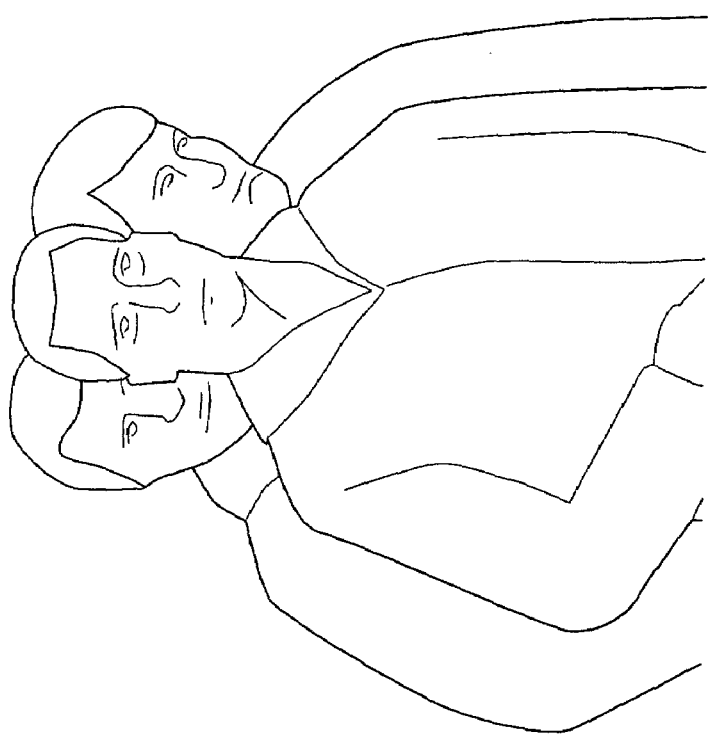

The detection of three live persons is shown in FIGS. 17A and 17B. A composite wavelength visible light image is shown in FIG. 17A. The pixels that are classified as live are displayed in FIG. 17B in red (shown as vertical hatching). Spatial feature information can be used in addition to liveness detection to aid in counting the number of individuals.

Figure 18:
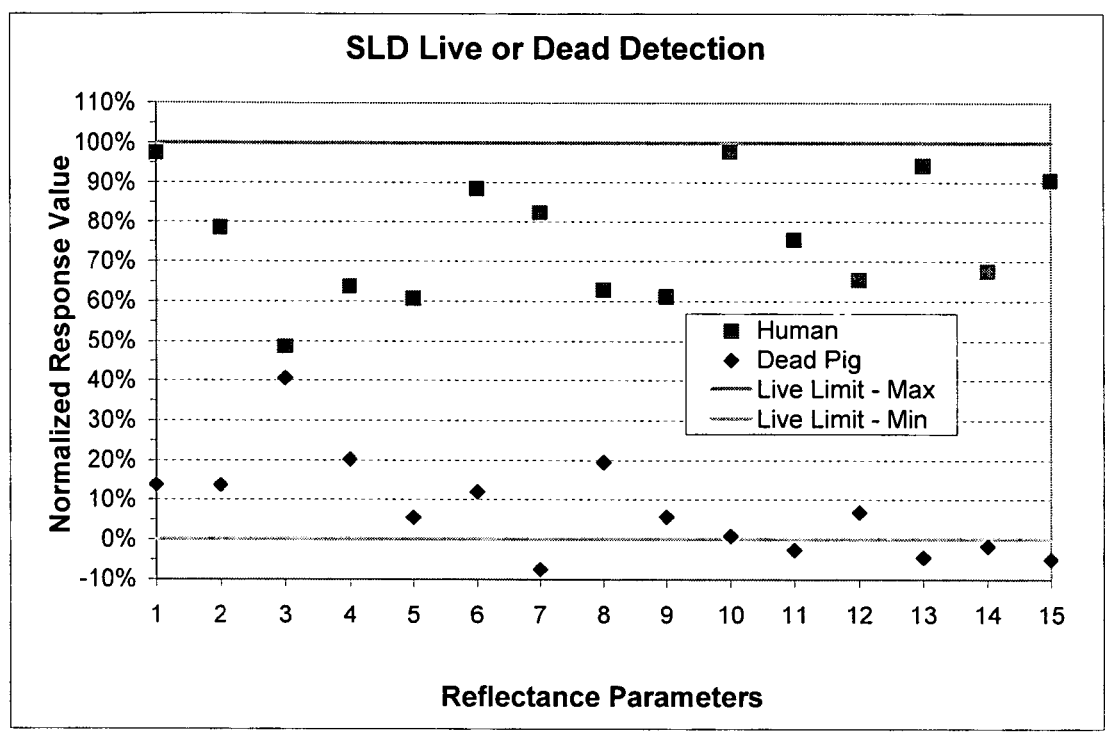
FIG. 18. Results of liveness detection with a portable viewer apparatus performed with pigs as subjects.

Tests of the liveness detection with a non-imaging viewer apparatus have been performed with pigs as subjects. Because pigs and humans have skin that is very similar, pig skin is frequently used as a surrogate for human skin in research. The liveness detection method and spectral liveness detector (SLD) viewer were used to detect live and dead pigs. The results are shown in FIG. 18. After slaughter, the dead pig skin was viewed and detected as dead by the method and viewer. The chart shows the normalized ratios of intensity values for 15 ratios of pairs of intensities measured as the differences of logarithmic amplifier outputs (hence the possibility of negative values of the ratios) at six wavelengths (450, 500, 550, 600, 650, 750 nm), which correspond to oxygenated hemoglobin and water. A typical live human data set is shown with the maximum and minimum liveness limits for all data. Data for live pigs (not shown) are very similar to data for humans. The dead pig data set clearly shows points that are below the liveness range (live limit—minimum) and so correspond to a 'not-live' determination. Furthermore, the data points of the data sets for live subjects typically are greater than the data points for dead subjects as shown in the example. The "Reflectance Parameters", numbered 1-15, in the graph of FIG. 18 are the ratios of the logarithmic amplifier outputs for the various wavelengths.

From the foregoing description, various modifications and changes in the design and method will occur to those skilled in the art without varying from the scope of the invention as defined in the following claims.

What is claimed is:

1. A method for remotely detecting whether a subject is alive, comprising the steps of:
    determining a calibration spectral signature for light reflectance from living skin;
    normalizing the calibration spectral signature values to the calibration reflectance value at a reference wavelength;
    storing the normalized calibration spectral signature;
    determining a subject spectral signature of the light reflectance of a region of skin of the subject whose liveness is to be determined;
    normalizing the subject spectral signature values to the subject reflectance value at the reference wavelength;
    comparing the normalized subject spectral signature with the normalized calibration spectral signature for at least one wavelength;
    generating a subject liveness signal based on the comparison of the normalized subject spectral signature with the normalized calibration spectral signature; and
    emitting the subject liveness signal.

2. The method of claim 1 wherein determining a calibration spectral signature comprises collecting a spectral signature from a known live subject under lighting conditions that are substantially the same as those present when determining the test spectral signature.

3. The method of claim 1 wherein the light has a wavelength in a range from approximately 400 nm to approximately 700 nm.

4. The method of claim 1 wherein the reference wavelength is approximately 530 nm.

5. The method of claim 1 wherein generating a subject liveness signal further comprises generating a first signal indicating that the subject is live if the test spectral signature substantially coincides with the calibration spectral signature, and otherwise generating a second signal that the subject is not live if the test spectral signature does not substantially coincide with the calibration spectral signature.

6. The method of claim 1 wherein the at least one wavelength is at least 450 nm and less than or equal to 480 nm.

7. The method of claim 1 wherein the at least one wavelength is at least 600 nm and less than or equal to 700 nm.

8. An apparatus for remotely detecting whether a subject is alive, comprising:
    a viewer and an analyzer;
    wherein the viewer comprises:
        an objective and a beamsplitter which together form a first intermediate image and a second intermediate image;
        a reticle placed in the plane of the first intermediate image;
        an eyepiece for viewing the first intermediate image through the reticle;
        an optical fiber bundle comprising a plurality of sub-bundles, a first end of the optical fiber bundle being disposed in the plane of the second intermediate image such that the plurality of sub-bundles splits a central region of the second intermediate image into a plurality of light signals; and
        a sensor comprising at least one photodiode assembly, wherein at least one optical fiber sub-bundle is optically coupled to the photodiode assembly;
    wherein the analyzer comprises: a digital signal processor and a memory, such that the digital signal processor generates a liveness signal if a normalized subject spectral signature is substantially equivalent to a normalized calibration spectral signature template stored in the memory and otherwise generates a not live signal.

9. The apparatus of claim 8 wherein the normalized calibration spectral signature is determined from reflectance measurements of a living human skin.

10. The apparatus of claim 8 wherein each of the plurality of light signals transmitted by the plurality of sub-bundles of optical fibers has an approximately equal intensity.

11. The apparatus of claim 8 wherein the first intermediate image comprises light that is transmitted through the beamsplitter and the second intermediate image comprises light that is reflected from the beamsplitter.

12. The apparatus of claim 11 wherein the beamsplitter reflects wavelengths of light used for detecting whether a subject is alive.

13. The apparatus of claim 11 wherein the beamsplitter transmits light having wavelengths in the range of approximately 500 nm to approximately 540 nm.

14. The apparatus of claim 8 wherein the reticle has a centrally-located reference circle for locating a region of a subject, the reference circle being optically conjugated with the first end of the optical fiber bundle such that the light transmitted to the photodiode assembly is from substantially the same region of the subject as is located within the reference circle.

15. The apparatus of claim 8 wherein the photodiode assembly comprises a lens, an optical bandpass filter, and a preamplifier, wherein the lens focuses light from an optical fiber sub-bundle through the optical bandpass filter and preamplifier onto the photodiode.

16. The apparatus of claim 15, wherein the center wavelength of the bandpass filter is optimized for the detection of difference between spectral signatures of living and dead human skins.

17. The apparatus of claim 8 wherein the optical fiber bundle is non-coherent.

18. The apparatus of claim 8 wherein the viewer further comprises a first light emitting diode optically coupled to the reticle by a first optical fiber, wherein the first light emitting diode transmits the liveness signal to the reticle.

19. The apparatus of claim 18 wherein the view further comprises a second light emitting diode optically coupled to the reticle by a second optical fiber, wherein the second light emitting diode transmits the not live signal to the reticle.

20. An apparatus for remotely detecting whether a subject is alive, comprising:

a hyperspectral imaging system comprising at least one camera for collecting a plurality of subject images formed by photons reflected from the subject, each image representing photons having wavelengths within a sub-portion of the electromagnetic spectrum;

an image processor comprising memory for storing a reference spectral signature image, and logic circuits for comparison of the subject images to the reference spectral signature image to determine whether the subject is alive, wherein the reference spectral signature image comprises an image collected from a known live sample by the hyperspectral imaging system and sent to the memory; and an output device to indicate whether the subject is alive.

21. The apparatus of claim 20 wherein the output device comprises a display monitor for presenting an image of the subject showing sub-portions of the subject that are determined to be alive.

22. The apparatus of claim 20 wherein the output device comprises a light emitting diode.

23. The apparatus of claim 20 wherein the hyperspectral imaging system further comprises a liquid crystal tunable filter for selectively transmitting photons having wavelengths within a sub-portion of the electromagnetic spectrum to the camera.

24. The apparatus of claim 23 wherein the liquid crystal tunable filter transmits photons having wavelengths within an approximately 20 nm width band of the electromagnetic spectrum to the camera.

25. The apparatus of claim 20 wherein the hyperspectral imaging system further comprises a acousto-optical tunable filter for selectively transmitting photons having wavelengths within a sub-portion of the electromagnetic spectrum to the camera.

26. The apparatus of claim 20 wherein the comparison of the subject images to the reference spectral signature image is performed using a technique selected from the group consisting of: least squares analysis; spectral angle mapping; and artificial neural network analysis.

27. A method for remotely detecting whether a subject is alive, comprising the steps of:

determining a calibration spectral signature for light reflectance from living skin;

storing the calibration spectral signature;

determining a subject spectral signature of the light reflectance of the subject whose liveness is to be determined, wherein the subject spectral signature is collected as an image comprising a plurality of pixels;

comparing the subject spectral signature with the calibration spectral signature;

generating a subject liveness signal for each pixel of the image, based on the comparison of the subject spectral signature for each pixel with the calibration spectral signature; and displaying the subject liveness signal.

28. The method of claim 27 wherein collecting an image of the subject spectral signature comprises hyperspectral imaging.

29. The method of claim 28 wherein comparing the subject spectral signature with the calibration spectral signature comprises a technique selected from the group consisting of: least squares analysis; spectral angle mapping; and artificial neural network analysis.

30. The method of claim 28 wherein hyperspectral imaging is performed using wavelengths in the range of approximately 400 nm to approximately 1700 nm.

31. The method of claim 28 wherein hyperspectral imaging is performed using wavelengths in a range of approximately 1000 nm to approximately 1600 nm.

32. The method of claim 27 wherein determining a calibration spectral signature for light reflectance from living skin comprises averaging spectral signatures from a plurality of living human skin samples.

33. The method of claim 27 further comprising:
using the subject liveness signal to identify live individuals in a crowd.

34. The method of claim 27 further comprising:
using the subject liveness signal in conjunction with another biometric indicator to determine whether the subject is wearing a disguise.

35. The method of claim 27 further comprising:
using the subject liveness signal to track a moving subject.

* * * * *